(12) United States Patent
Yayon et al.

(10) Patent No.: US 6,730,666 B1
(45) Date of Patent: May 4, 2004

(54) PHARMACEUTICAL COMPOSITIONS COMPRISING PORPHYRINS AND SOME NOVEL PORPHYRIN DERIVATIVES

(75) Inventors: Avner Yayon, Moshav Sitria (IL); David Aviezer, Hashmonaim (IL); Zeev Gross, Petach Tikva (IL)

(73) Assignees: Yeda Research and Development Co. Ltd., Rehovot (IL); Technion Research and Development Foundation Ltd., Haifa (IL)

( * ) Notice: Subject to any disclaimer, the term of this patent is extended or adjusted under 35 U.S.C. 154(b) by 0 days.

(21) Appl. No.: 09/831,305

(22) PCT Filed: Nov. 8, 1999

(86) PCT No.: PCT/IL99/00602

§ 371 (c)(1),
(2), (4) Date: Jul. 18, 2001

(87) PCT Pub. No.: WO00/27379

PCT Pub. Date: May 18, 2000

(30) Foreign Application Priority Data

Nov. 8, 1998 (IL) .................................. 126953

(51) Int. Cl.⁷ ........................ A61K 38/41; C07D 487/22
(52) U.S. Cl. ........................ 514/183; 514/185; 534/10; 540/121; 540/145; 540/465; 540/471; 540/474
(58) Field of Search ................. 514/183, 185; 540/121, 145, 465, 471, 474; 534/10

(56) References Cited

U.S. PATENT DOCUMENTS

| | | | |
|---|---|---|---|
| 4,658,023 A | 4/1987 | Shudo | 514/185 |
| 5,236,914 A | 8/1993 | Meunier et al. | 514/185 |
| 5,268,371 A | 12/1993 | Mauclaire et al. | 514/185 |
| 5,272,142 A | 12/1993 | Sessler et al. | 514/185 |
| 5,284,647 A | 2/1994 | Niedballa et al. | 424/81 |
| 5,576,013 A | 11/1996 | Williams et al. | 424/423 |

FOREIGN PATENT DOCUMENTS

| | | |
|---|---|---|
| EP | 0 213 272 B1 | 4/1986 |
| EP | 0 330 799 A1 | 9/1989 |
| EP | 0 345 171 A1 | 12/1989 |
| FR | 2 656 866 A1 | 7/1991 |
| JP | 62-161725 | 7/1987 |
| WO | WO 89/11277 A2 | 11/1989 |
| WO | WO 93/02192 A1 | 2/1993 |
| WO | WO 94/12239 A1 | 6/1994 |
| WO | WO 95/24930 A1 | 9/1995 |
| WO | WO 95/31197 A1 | 11/1995 |
| WO | WO 96/05862 A1 | 2/1996 |
| WO | WO 98/15128 A2 | 5/1996 |
| WO | WO 98/33503 A1 | 8/1998 |
| WO | WO 00/09111 A2 | 2/2000 |

OTHER PUBLICATIONS

Driaf et al, "Glycosylated Cationic Porphyrins as Potential Agents in Cancer Phototherapy", *Tetrahedron Letters* 34(6):1027–1030 (1993).

Jori et al, "Controlled targeting of different subcellular sites by porphyrins in tumor–bearing mice", *Br J Cancer* 53:615–621 (1986).

Neya et al, "An Improved Synthesis of Corrole", *Tetrahedron Letters* 38(23):4113–4116 (1997).

Packer et al, "Hematoporphyrin Photoradiation Therapy", *Arch Opthamol* 102:1193–1197 (1984).

Whelhouse et al, "Cationic Porphyrins as Telomerase Inhibitors: the interaction of Tetra–N–methyl–4–pyridyl)porphine with Quadruplex DNA" *J Am Chem Soc* 120:3261–3262 (1998).

*Primary Examiner*—John M. Ford
(74) *Attorney, Agent, or Firm*—Browdy and Neimark

(57) ABSTRACT

Tertrapyrrolic macrocycles selected from 5,10,15,20-tetraaryl-porphyrins and 5,10,15-triaryl-corrloes, wherein said aryl radical is a carboaryl, a heteroaryl or a mixed carboaryl-heteroaryl radical and at least two of said aryl radicals are positively charged, inhibit growth factor (e.g. bFGF, VEGF) receptor tyrosine kinase activity, and are useful for inhibition of cell proliferation mediated by growth factor receptor tyrosine kinase activity for example for inhibition of angiogenesis, or vascular smooth muscle cell proliferation in disorders including atherosclerosis, hyperthrophic heart failure and postsurfical restenosis, and of cell proliferation and migration in the treatment of primary tumors and metastasis. Some of the 5,10,15,20-tetraarylprophyrins are novel compounds.

34 Claims, 16 Drawing Sheets

PHARMACEUTICAL COMPOSITIONS COMPRISING PORPHYRINS AND SOME NOVEL PORPHYRIN DERIVATIVES

REFERENCE TO RELATED APPLICATIONS

The present application is the national stage under 35 U.S.C. 371 of international application PCT/IL99/00602, filed Nov. 8, 1999 which designated the United States, and which international application was published under PCT Article 21(2) in the English language.

FIELD OF THE INVENTION

The present invention relates to inhibition of growth factor tyrosine kinase receptor activity, particularly inhibition of angiogenesis and related disorders, tumor progression and growth factor related skeletal disorders, by porphyrin and corrole compounds, and to certain novel porphyrin compounds.

ABBREVIATIONS: AP, alkaline phosphalase; EGF, epidermal growth factor; bFGF, basic fibroblast growth factor; FGF, fibroblast growth factor, FGFR, FGF receptor, FGFR-1, FGF receptor-1; FGFR-3, FGF receptor-3; UP, FGFR-1-alkaline phosphatase fusion protein; FR3-AP, FGFR-3-alkaline phosphatase fusion protein; HB-EGF, heparin-binding EGF-like growth factor; HGF, hepatocyte growth factor, HSPG, heparan sulfate proteoglycans; IGF, insulin-like growth factor, LLC, Lewis Lung Carcinoma; NGF, nerve growth factor, PDGF, plateleterived growth factor; SMC, smooth muscle cells; TKR, tyrosine kinase receptor; VEGF, vascular endothelial growth factor, VSMC, vascular smooth muscle cells.

BACKGROUND OF THE INVENTION

Growth factors play a pivotal role in the multistep pathway of cell differentiation and migration, tumor and metastasis progression, and angiogenesis.

The pathological mechanism of many proliferative diseases is determined by biological events such as growth factor receptor stimulation, autophosphorylation, and the phosphorylation of intracellular protein substrates.

Phosphorylation of tyrosine residues on protein substrates in normal cells serves a critical function in intracellular growth signaling pathways initiated by stimulated extracellular growth factor receptors. Growth factors such as fibroblast growth factor (FGF), epidermal growth factor (EGF), platelet-derived growth factor (PDGF), nerve growth factor (NGF), vascular endotheial growth factor (VEGF) and hepatocyte growth factor (HGF), associate with their respective extracellular receptors thus activating the intracellular tyrosine kinase domains of said receptors and catalyzing the phosphorylation of the receptors themselves (autophosphorylation) or of intracellular substrates. This association between the growth factor ligand and the respective receptor simulates tyrosine kinase activity as one of the initial biochemical events leading to DNA synthesis and cell division Therefore, compounds which inhibit protein tyrosine kinases associated with intracellular growth factor signal transduction pathways may be useful for the treatment of cellular proliferative disorders.

Fibroblast growth factors (FGFs) are abundant m normal and malignantly transformed cells and play a pivotal role in the multistep pathway of malignant transformation, tumor progression, metastasis and angiogenesis. In adults, bFGF, as well as the FGF oncogenes HST (FGF4) and int-2 (FGF-3) are found in tumors such as stomach cancer, Kaposi's sarcoma, melanoma and breast cancer.

FGFs bind avidly to the glycosaminoglycan heparin and to heparan sulfate proteoglycans (HSPG) found on cells and in the extracellular matrix. Studies on the mode of action of FGFs identified a novel role for beparin-like molecules in the formation of distinct FGF-heparin complexes that are essential for binding of FGF to its cognate receptor (Yayon et al, 1991; Rapraeger et al, 1991). We and others have recently addressed the importance of specific heparin and heparan sulfate structures in FGF receptor binding activity (Guimond et al, 1993; Aviezer et al, 1994a) and have demonstrated that specific HSPGs such as perlecan, function as a low affinity, accessory receptor for bFGF and as a potent angiogenic modulator (Aviezer et al, 1994b).

FGF receptors were found to play a role in genetically acquired growth disorders. Thus, a number of mutations in FGF receptors have been implicated in various forms of human skeletal dysplasias. For instance, achondroplasia, the most common form of human dwarfism, is caused by a pecfic mutation in the transmembrane domain of FGFR-3 (Rousseau et al, 1994; Shiang et al, 1994). Other skeletal disorders such as Crouzon's syndrome and thanatophoric dysplasia, involve mutations in the extracellular domain (Reardon et al, 1994) or the kinase domain of FGF receptors. In achondroplasia, a point mutation (Gly-380/Arg) in the transmembrane domain of FGFR-3 leads to impaired growth. Since we have identified FGF-9 as a putative ligand for FGFR-3 (Hecht et al, 1995), it is conceivable that strategies aimed at check points along the biochemical mechanism of the FGFR-3 activation pathway, may result in treatment of achondroplasia Naski et al, 1996, have demonstrated that both the achondroplasia and thanatophoric dysplasia mutations constitutively activate the receptor as evidenced by receptor tyrosine phosphorylation. These findings have been biologically supported by knock out of the FGFR-3 gene (Deng et al, 1996). Furthermore, it seems that FGFRs are involved in bone and cartilage benign tumors, such as hereditary multiple exostosis, osteoarthritis and others. Exostosis is an osteocartilaginous benign tumor of an autosomal dominance, diversed phenotype and heterogeneous genetics characterized by the formation of cartilaginous capped metaphyseal bony protrusions.

Vascular endothelial growth factor (VEGF) is a known endothelial mitogen and a potent enhancer of vascular permeability. VEGF is a multifunctional cytoline that exerts in vivo a key role in physiological and pathological neoangiogenesis by stimulating endothelial cell proliferation and vessel hyperpermeability, VEGF exists as one of four different isoforms, respectively, VEGF 121, VEGF 165, VBGF 199, and VEGF 206. VEGF121 does not bind heparin while the other three isoforms do, and it has been documented that the binding of VEGF165 to its receptor is dependent upon cell surface heparin suite proteoglycans (Gitay-Goren et al, 1992). VEGF binds to Flt-1 and Flk-1/KDR cell membrane receptors which are members of the tyrosine kinase receptor family. VEGF seems to be a crucial mediator of physiological neoangiogenesis during the embryonic development and the female cycle.

VEGF also has a major role in the pathogenesis of many diseases including hypervascularized tumors, rheumatoid arthritis, cutaneous diseases and proliferative retinopathies. VEGF gene expression in vitro is enhanced approximately ten times by hypoxia. Current evidence (Patt et al, 1998) suggests that hypoxia is also the driving force for VEGF gene expression in cells in vivo and represents the most important trigger for tumor angiogenesis and edema. Recent approaches to inhibit tumor angiogenesis and metastasis formation concentrate on the disruption of VEGF/VEGF receptor signal transduction pathway in vivo. Persistent angiogenesis may cause or exacerbate certain diseases such as psoriasis, rheumatoid arthritis, hemangiomas, angiofibromas, diabetic retinopathy and neovascular glaucoma. An inhibitor of VEGF activity would be useful as a treatment for such diseases and other VEGF-induced pathological angiogenesis and vascular permeability conditions, such as tumor vascularization.

The EGF receptor, which main ligands are EGF, HB-EGF and transforming growth factor α (TGF-α), is involved in the disease processes of many malignant tumors, especially colon and breast cancers. Overexpression and mutation of the closely related Erb-2 and Erb-3 receptors have been shown to be the major risk factors in poor prognosis of breast cancer. HB-EGF is a most potent activator of the EGF receptor on smooth muscle cells (SMC), including VSMC, playing a crucial role in the pathogenesis of atherosclerosis and benign hypertrophy of the uterus and the formation of leiomyomas (tumors composed of nonstriated muscular tissue).

PDGF has been identified as a potent endogenous vascular smooth muscle cells (VSMC) mitogen and chemoattractant. Proliferation and directed migration of VSMC are important elements in processes such as vascular remodeling, atherosclerosis and restenosis. In balloon-injured rat model, elevated vascular mRNA expression of PDGF A and B chains and PDGF receptors has been observed in carotid arteries (J. Cell Biology, 1990, 111: 2149–2158) and infusion of PDGF greatly increased intimal thickening and migration of VSMC (J. Clin. Invest. 1992, 89: 507–511).

Hepatocyte growth factor (HGF), also known as scatter factor (SF), is the prototype of a family of structurally related soluble molecules (scatter factors), which also includes the HGF-lik/macrophage-stimulating protein (HGF1/MSP). HGF and HGF1/MSP control a complex genetic program known as 'invasive growth' which leads to cell dissociation, proliferation, invasion of extracellular matrix, prevention of apoptosis, acquisition of polarity and tubule formation. HGF is synthesized by mesenchymal cells and is a paracrine effector of cells, predominantly epithelial, that express the Met tyrosine kinase receptor. The HGF and HGF1/MSP receptors are the tyrosine kinases encoded by the homologous genes met and ron. During development, coordinated control of invasive growth by HGF-Met is essential. Met and Ron receptor signalling occurs via a two-phosphotyrosine multifunctional docking site located in their C-terminal regions.

HGF is a pleiotropic cytokine known to be involved in tissue regeneration and repair (Van de Woude et al, 1997). HGF exerts mitogenic and motogenic effects in different cell types. One of the mechanisms by which HGF exerts its antiproliferative effect is induction of apoptosis. HGF activation of Ras and phosphantidylinositol-3-kinase through the multifunctional docking site is required for receptor-mediated invasive growth. In a number of malignant tumours met and ron are mutated, amplified or overexpressed. Oncogenically activated met and ron confer transforming, invasive and metastatic properties to normal cells. Point mutations of the multifunctional docking site dissociate the transforming potential from the invasive-metastatic phenotype showing that distinct signalling pathways are involved. An increasing number of reports have implicated Met-HGF signalling in a variety of human cancers (Yanagawa et al, 1998).

Nerve growth factor (NGF) was characterized over 4 decades ago, and like the other neurotrophins subsequently discovered it is best known for its trophic role, including the prevention of programmed cell death in specific populations of neurons in the peripheral nervous system. This property can be accounted for by the activation of a tyrosine kinase receptor. NGF also regulates neuronal function, as illustrated by its role in pain and inflammation, and in synaptic plasticity. Numerous studies published in the last 10–15 years have shown that NGF, a polypeptide originally discovered in connection with its neurotrophic activity, also acts on cells of the immune system Finally, NGF recently was shown (Frade and Barde, 1998) to activate the neurotrophin receptor p75 (p75M), a receptor with no intrinsic catalytic activity and with similarities to members of the tumor necrosis factor receptor family. During normal development, the activation of p75NTR by NGF actually kills cells in the central nervous system (Frade and Barde, 1998). One remarkable property of NGF is then that it controls cell numbers in opposite ways in the developing nervous system, a result of its unique ability to activate two different receptor types. NGF has been found in various immune organs including the spleen, lymph nodes and thymus, and cells such as mast cells, eosinophils, and B and T cells (Aloe et al, 1997).

The circulating levels of NGF increase in inflammatory responses, in various autoimmune diseases, in parasitic infections, and in allergic diseases. Stress-related events both in animal models and in man also result in an increase of NGF, suggesting that this molecule is involved in neuroendocrine functions (Connor et al, 1998). The rapid release of NGF is part of an alerting signal in response to either psychologically stressful or anxiogenic conditions in response to homeostatic alteration. Thus, the inflammation and stess-induced increase in NGF might alone or in association with other biologic mediators induce the activation of immune cells during immunologic insults. Recent evidence suggests that neurotrophic factors that promote the survival or differentiation of developing neurons may also protect mature neurons from neuronal atrophy in the degenerating human brain. Furthermore, it has been proposed that the pathogenesis of human neurodegenerative disorders may be due to an alteration in neurotrophic factor and/or trk receptor levels. The use of neurotrophic factors as therapeutic agents is a novel approach aimed at restoring and maintaining neuronal function in the central nervous system (CNS).

Porphyrins have been of interest of chemists and medical scientists for over a century. It has been known for many years that porphyrins interact with neoplastic tumors and the fact that porphyrins demonstrate high affinity to tumorigenic cells in vitro and solid tumors in vivo, is well established (Dougherty et al, 1998: Jori et al, 1986).

Porphyrin derivatives have been disclosed for the treatment of tumors, cancers and malignant tissues in combination with electromagnetic radiation or radioactive emissions. Since they absorb light strongly in the 690–880 nm region, many porphyrins were suggested for use as photosensitizers in photodynamic therapy (PDT). See, for example, U.S. Pat. Nos. 5,268,371 and 5,272,142, European Patent Nos. 213272 and 584552 and Jori et al. (1986).

Some porphyrin derivatives have been disclosed for use in combination with electromagnetic radiation or radioactive emissions for inhibiting angiogenesis. See, for example, the PCT publications WO 95/24930, WO 94/12239 and WO 93/02192 and U.S. Pat. Nos. 5,576,013 and 5,284,647. Some publications suggested the use of porphyrin derivatives as anti-tumor agents in the absence of electromagnetic radiation or radioactive emission based on their ability to cleave DNA (U.S. Pat. No. 4,658,023 and U.S. Pat. No. 5,236,914).

The porphyrins disclosed in U.S. Pat. No. 5,236,914 always include a central Fe or Mn metal atom and may be substituted by 1 to 3 positively charged N-alkyl-pyridylium groups.

Corroles are slightly contracted porphyrins. The corroles are much less known than porphyrins and their synthesis is very complex. The first corrole was reported in 1965. A simple procedure for corrole synthesis is the subject of Israel Patent Application No. 126426. Neither this patent application nor any other publication disclose or suggest any pharmaceutical application of corroles.

None of the foregoing references teach or suggest that the porphyrin and corrole compounds of the compositions of the present invention inhibit growth factor receptor tyrosine kinase (RTK) activity.

DESCRIPTION OF THE INVENTION

It has now been found, according to the present invention, that certain porphyrin and corrole compounds can inhibit growth factor receptor tyrosine kinase (RTK) activity.

The present invention thus relates, in one aspect, to a pharmaceutical composition for inhibiting growth factor receptor tyrosine kinase (RTK) activity comprising a tetrapyrrolic macrocycle selected from a. 5,10,15,20-tetraaryl-porphyrin and a 5,10,15-triaryl-corrole, wherein said aryl radical is a carboaryl, a heteroaryl or a mixed carboaryl-heteroaryl radical and at least two of said aryl radicals are positively charged, and a pharmaceutically acceptable carrier.

The growth factor RTK whose activity is inhibited by the compositions of the invention may be fibroblast growth factor (FGF) RTK, epidermal growth factor (EGF) RTK, heparin-binding EGF-like growth factor (HB-EGF) RTK, platelet-derived growth factor (PDGF) RTK, vascular endothelial growth factor (VEGF) RTK, nerve growth factor (VGF) RTK, hepatocyte growth factor (HGF) RTK, insulin RTK and insulin-like growth factor (IGF) RTK.

All fibroblast growth factor receptors are encompassed by the invention but particularly FGFR-1 and FGFR-3 are envisaged, which ligands are, among others, bFGF and FGF9, respectively.

In one aspect, the pharmaceutical compositions of the invention are used for inhibition of cell proliferation mediated by growth factor RTK activity. In one embodiment of this aspect, the compositions are used for inhibition of angiogenesis or neovascularization by particularly inhibiting the binding of VEGF to a VEGF receptor. The treatment of a condition characterized by excess of undesired angiogenesis with such a composition is not accompanied by any added electromagnetic radiation having a frequency absorbed by the porphyrin or corrole derivative or any radioactive emissions from said derivatives. Preferred compounds according to the invention for treatment of angiogenesis are the porphyrin herein designated P1 and the corrole herein designated P21.

In another embodiment of this aspect, the compositions are used for inhibition of vascular smooth muscle cell proliferation in disorders including atherosclerosis, hyperthrophic heart failure and postsurgical restenosis.

Restenosis after successful percutaneous transluminal coronar angioplasty (PTCA) remains a major problem despite great improvement in the technique, use of certain drugs and stents implantation. Heparin-binding growth factors (HBGF), mainly the FGFs and HB-EGF, play a crucial role in the pathogenesis of restenosis by enhancing medial smooth muscle cells (SMC) migration and proliferation and subsequently neo-intima formation The FGF antagonists comprised in the compositions of the present invention interfere with the interaction between HBGF and their receptors and exert a marked inhibitory effect on SMC proliferation as shown by direct cell proliferation assays and reduced thymidine incorporation, as well as by direct inhibition of high affinity basic FGF in vitro and on cells. The inhibitors block ligand-receptor interaction by competitively inhibiting the essential association between both ligand and receptor with heparan sulfates and in a dose-dependent manner. According to the invention, porphyrin compounds P1 and P20 were found particularly active in the prevention of restenosis after PTCA by specifically inhibiting SMC proliferation and luminal narrowing by the neo-intima.

In another embodiment of this aspect, the compositions of the invention are used for inhibition of cell proliferation and migration in the treatment of primary tumors and metastasis. The inhibition of tumor growth and metastasis, processes in which bFGF appears to play a pivotal role, was tested both in vitro and in vivo with the porphyrins and corroles. A clear inhibition of primary tumor formation in nude mice model and of primary tumor growth and metastasis in C57 black mice injected with LLC could be observed, particularly with the compounds herein designated P1, P5, P7, P20 and P21.

In another embodiments of this aspect, the compositions of the invention are used for treatment of nonmalignant tumors such as benign prostate hyperthrophy, diabetic retinopathy, psoriasis, rheumatoid arthritis, and other disorders including retrolental fibroplasia, macular degeneration, hemangioma, arteriovenous malformation, hypertrophic scars, acne, scleroderma and autoimmune diseases.

In another aspect, the pharmaceutical compositions of the invention are used for treatment of bone and cartilage related disorders including inherited skeletal disorders such as achondroplasia, dwarfism, craniosyuostosis. According to the invention, the compounds, and particularly the porphyrin herein designated P16, were found to inhibit the binding of FGF9 to FGFR-3, indicating that they can be useful for treating FGFR-3 related growth disorders such as achondroplasia The pharmaceutical composition of the invention comprises particularly a 5,10,15,20-tetaaryl-porphyrin of the formula:

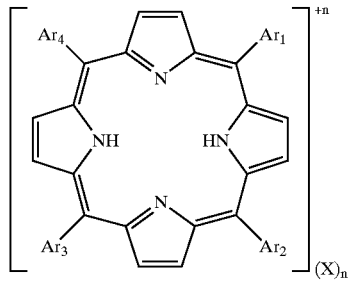

wherein $Ar_1$, $Ar_2$, $Ar_3$, and $Ar_4$, the same or different, are each an aryl radical selected from a carboaryl, a heteroaryl and a mixed carboaryl-heteroaryl radical, at least two of said aryl radicals being positively charged, n is an integer from 2 to 4 and X is a pharmaceutically acceptable anion, or a 5,10,15-triaryl-corrole of the formula:

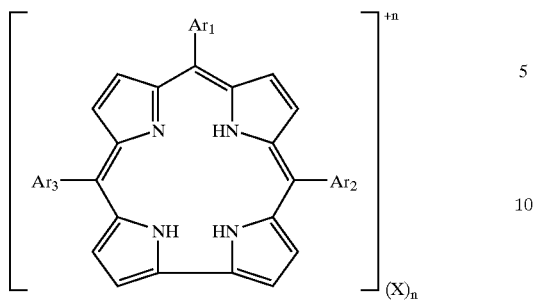

wherein $Ar_1$, $Ar_2$, and $Ar_3$, the same or different, are each an aryl radical selected from a carboaryl, a heteroaryl and a mixed carboaryl-heteroaryl radical, at least two of said aryl radicals being positively charged, n is an integer from 2 to 3 and X is a pharmaceutically acceptable anion.

As defined herein, the carboaryl radical, by itself or as part of the mixed carboaryl-heteroaryl radical, is a substituted monocyclic or bicyclic aromatic radical and the heteroaryl radical, by itself or as part of the mixed carboaryl-heteroaryl radical, is a substituted 5–6 membered aromatic ring containing 1–3 heteroatoms selected from O, S and/or N.

The carboaryl radical may be phenyl, biphenyl or naphthyl substituted by one or more radicals including, but not being limited to, halogen, alkyl, alkoxy, alkylamino, aminoalkylamino, and trialkylammonium, wherein the alkyl radical may have from 1 to 8, preferably 1–4, carbon atoms. The halogen may be chloro or, preferably, fluor. The carboaryl radical may be a phenyl radical substituted by fluoro such as, for example, pentafluorophenyl, or by $tri(C_1$–$C_8)$ alkylammonium, for example, 4trimethylammoniophenyl, or it may have different substituents, for example, amino $(C_1$–$C_8)$alkylamino-tetrafluorophenyl, e.g. aminopropylamino-2,3,5,6 -tetrafluorophenyl, or $tri(C_1$–$C_8)$ alkylammonium-tetrafuorophenyl, for example, 4trimethylammoniophenyl-2,3,5,6-tetrafluorophenyl.

The heteroaryl radical may be a 5–6 membered aromatic ring containing 1–3 heteroatoms selected from O, S and/or N including, but not being limited to, furyl, thienyl, pyrrolyl, imidazolyl, thiazolyl, pyridyl, pyrimidyl and triazinyl, substituted by one or more radicals including, but not being limited to, halogen, alkyl, alkoxy, alkylamino, aminoalkylamino, and trilkylammonium. Examples of such heteroaryl radicals are $N$-$(C_1$–$C_8)$alkyl-pyridylium, preferably 2-; 3- or 4-(N-methyl) pyridylium.

An example of a mixed carboaryl-heteroaryl radical according to the invention is N-(Cl-Cg)alkyl-pyridylium-tetrafluorophenyl, for example, 4-N-methyl-2-pyridylium)-2,3,5,6-tetrafluoro-phenyl and the corresponding 3- and 4-(N-methyl) pyridylium compounds.

The anion $X^-$ according to the invention is a halide, preferably $I^-$, or a pseudo halide anion, or the anion of a carboxylic or sulfonic acid, for example from alkyl sulfonate, trifluoromethyl sulfonate or tosyl (p-toluene sulfonic acid).

Some of the porphyrins used in the present invention are known and either are commercially available or can be prepared by known procedures. P1–P5, for example, are commercially available, and P15, for example, can be prepared according to La et al, 1999.

In another aspect, the invention relates to novel 5,10,15, 20-tetraaryl-porphyrins of the formula:

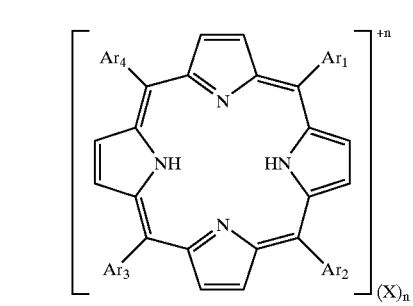

wherein $Ar_1$, $Ar_2$, $Ar_3$, and $Ar_4$, the same or different, are each an aryl radical selected from a carboaryl, a heteroaryl and a mixed carboaryl-heteroaryl radical, at least two of said aryl radicals being positively charged, n is an integer from 2 to 4 and X is a pharmaceutically acceptable anion, and wherein at least one of the non-positively charged aryl radicals, if present, is pentafluorophenyl or 4-amino($C_1$–$C_8$)alkylamino-2,3,5,6-tetrafluorophenyl, and at least two of the positively charged aryl radicals are N-($C_1$–$C_8$)alkyl-pyridylium or 4-N($C_1$–$C_8$)alkyl-pyridylium-2,3,5,6-tetrafluorophenyl, particularly 4-(N-methyl-2-pyridylium)-2,3,5, 6-tetrafluoro-phenyl, 4-(N-methyl-3-pyridylium)-2,3, 5,6-tetrafluoro-phenyl or 4-(N-methyl-4-pyridylium)-2,3,5,6-tetrafluoro-phenyl.

The novel porphyrins of the invention include the compounds herein designated P16, P17, P18, P19 and P20, which formulas appear in Appendix A.

The novel porphyrins according to the invention corresponding to the general formula II:

II

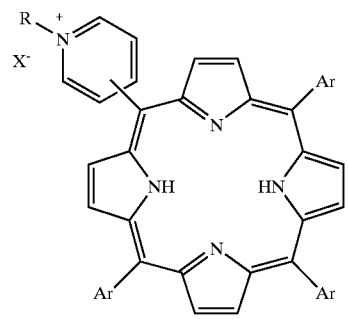

in which Ar represents:

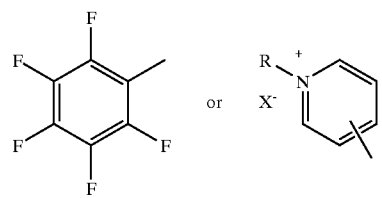

wherein the nitrogen atom (and the positive charge) is located at either the 2-, or 3-, or 4 position, and R represents $C_1$–$C_8$ linear or branched alkyl and $X^-$ represents a halide or pseudohalide anion, or the anion of a carboxylic of sulfonic acid, are prepared by a three-step method comprising:

a) condensation of pyrrole with a mixture of pentafluorobenzaldehyde and either 2-, or 3-, or 4-pyridinecarboxaldehyde in an acidic medium, such as to obtain a mixture of all possible substituted precursors in which the nitrogen atoms are tertiary and free of positive charges;

b) chromatographic separation of the above mentioned precursors by liquid chromatography. The relative amounts of each precursor are controlled in step (a), by adjusting the ratio of the appropriate pyridinecarboxaldehyde and pentafluorobenzaldebyde; and c) each of the purified precursors obtained in step (b), after optional protection of the inner nitrogens of the porphyrin ring by magnesium or zinc, is subjected to an alkylation reaction by means of either an allyl halide, or an alkyl tosylate, or an alkyl sulphonate.

The corrole compounds used in the present invention are prepared by the method described in Gross et al., 1999, which comprises solvent-free condensation of pyrrole with the appropriate aldehyde, followed by dehydrogenation and alkylation to obtain the desired salt.

In still another aspect, the present invention provides a pharmaceutical composition comprising a pharmaceutically acceptable carrier and a tetrapyrrolic macrocycle selected from a novel 5,10,15,20-tetraaryl-porphyrin as defined above and a 5,10,15-triaryl-corrole, wherein said aryl radical of the corrole compound is a carboaryl a heteroaryl or a mixed carboaryl-heteroaryl radical and at least two of said aryl radicals are positively charged. The novel porphyrins are preferably the compounds herein designated P16, P17, P18, P19 and P20, and the corrole is preferably the compound P21.

In a further aspect, the invention relates to a method for inhibiting growth factor receptor tyrosine kinase (RTK) activity comprising the administration of an inhibitor selected from a tetrapyrrolic macrocycle selected from 5,10,15,20tetraaryl-porphyrin and 5,10,15-triaryl-corrole, wherein said aryl radical is a carboaryl, a heteroaryl or a mixed carboaryl-heteroaryl radical and at least two of said aryl radicals are positively charged, in an amount sufficient to inhibit growth factor receptor activity.

The invention further relates to a method for inhibiting angiogenesis comprising the administration of an inhibitor selected from a tetrapyrrolic macrocycle selected from 5,10, 15,20-tetraaryl-porphyrin and 5,10,15-triaryl-corrole, wherein said aryl radical is a carboaryl, a heteroaryl or a mixed carboaryl-heteroaryl radical and at least two of said aryl radicals are positively charged, in an amount sufficient to inhibit angiogenesis.

The invention still further relates to a method for prevention of restenosis after percutaneous transluminal coronary angioplasty comprising the administration of an inhibitor selected from a tetrapyrrolic macrocycle selected from 5,10, 15,20-tetraaryl-porphyrin and 5,10,15-triaryl-corrole, wherein said aryl radical is a carboaryl, a heteroaryl or a mixed carboaryl-heteroaryl radical and at least two of said aryl radicals are positively charged, in an amount sufficient to inhibit smooth muscle cell proliferation. For this purpose, the selected porphyrin or corrole may be used also in a slow release mode by direct administration into the affected site in the vessel wall or as a chemical conjugate with locally implanted stents.

The invention also relates to a method for inhibiting primary tumor growth and metastasis comprising the administration of an inhibitor selected from a tetrapyrrolic macrocycle selected from 5,10,15,20-tetraaryl-porphyrin and 5,10,15-triaryl-corrole, wherein said aryl radical is a carboaryl, a heteroaryl or a mixed carboaryl-heteroaryl radical and at least two of said aryl radicals are positively charged, in an amount sufficient to inhibit primary tumor growth and metastasis.

The compositions of the present invention can be administered by any suitable mode of administration, e.g. orally or, preferably by injection, e.g. intravenously or subcutaneously, or by conjugation to locally implanted stents. The doses will depend on the condition of the patient and the disorder being treated and can be between 0.1 to 10 mg/kg/day, preferably from 1 to 5 mg/kg/day.

BRIEF DESCRIPTION OF THE DRAWINGS

FIGS. 1A–1C show inhibition of bFGF binding to the receptor FGFR-1 by the compound 5,10,15,20-tetrakis(N-methyl-4-pyridylium)-21H,23H-porphine tetra-p-tosylate, herein designated P1 or TMPP, wherein:

FIG. 1A shows the inhibitory effect of P1/TMPP on soluble FGFR-1 alkaline phosphatase fusion protein (FRAP) binding to bFGF immobilized on heparin. The binding was carried out as described in Methods, section (ii). The alkaline phosphatase (AP) enzymatic activity measured at 405 nm represents the level of FRAP binding;

FIG. 1B shows the inhibitory effect of P1/TMPP on $^{125}$I-bFGF binding to immobilized FRAP. The binding was carried out as described in Methods, section (iii). Results represent the mean value in one of at least two independent experiments; and FIG. 1C shows the inhibitory effect of P1/TMPP on the binding of $^{125}$I-bFGF to CHO cells transfected with FGFR-1. The binding was carried out as described in Methods, section (iv). Non-specific binding was determined in the presence of 100-fold excess of unlabeled bFGF ligand, and did not exceed 20% of the total bound ligand.

FIGS. 8A–8B show inhibition of bFGF binding to FGFR-1 wherein: FIG. 8A shows the effect of P1, P15–18 on soluble FGFR-1 alkaline phosphatase fusion protein (FRAP) binding to bFGF immobilized on heparin carried out, as described in FIG. 1A; and FIG. 8B shows the effect of P1, P20 and P21 on $^{125}$I-bFGF binding to immobilized FRAP, carried out as described in FIG. 1B.

FIGS. 10A–10B show the effect of porphyrins on the binding of VEGF to its receptors, wherein:

FIG. 10A shows the effect of P1 on the binding of $^{125}$I-VEGF to endothelial cells transfected with the VEGF receptor KDR. Binding of $^{125}$I-VEGF to confluent monolayers of endothelial cells expressing KDR was performed as described in Methods, section (x), in the presence of increasing concentrations of P1 and of unlabeled VEGF; and FIG. 10B shows the effect of porphyrins P1, P7, P15, P16 and P18 on soluble VEGF receptor flt-1-AP fusion protein binding to VEGF mobilized to heparin, carried out as described in Methods, section (ix).

DETAILED DESCRIPTION OF THE INVENTION

Figure 1A:
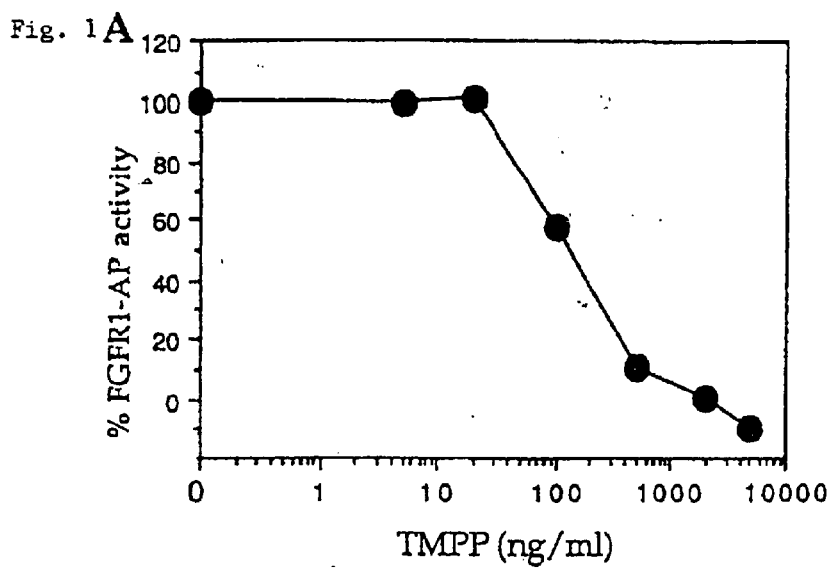

Fibroblast growth factors (FGF) and vascular endothelial growth factor (VEGF) play a pivotal role in the multistep pathway of malignant transformation, tumor progression, metastasis and angiogenesis. According to the present invention, 5,10,15,20-tetrakis (methyl-4-pyridyl)-21H,23H-porphine tetra-p-tosylate salt (TMPP or Compound P1), a member of the porphyrin molecule family, was identified as a potent inhibitor of basic FGF (GF-2, bFGF) binding to FGF receptor and activation. P1 demonstrated potent inhibition of binding of soluble FGF receptor 1 (FGFR-1) to bFGF immobilized on heparin at an IC$_{50}$ of 90 μM. P1 also inhibited direct binding of radiolabeled bFGF to FGFR in a cell free system as well as the binding to cells genetically engineered to express FGFR-1.

Furthermore, P1 also inhibited the binding of VEGF to its tyrosine kinase receptor in a dose-dependent manner. In an in vitro angiogenic assay measuring the extent of endothelial cell growth and tube formation and sprouting, P1 dramatically reduced the extent of the bFGF-induced endothelial cell outgrowth and differentiation, processes in which bFGF and VEGF play a pivotal role. In a Lewis lung carcinoma model, mice having received P1 showed a marked inhibition of both primary tumor progression and lung metastases development, with nearly total inhibition of the metastatic phenotype upon alternate daily injections of P1 at 25 μg/g of body mass. Also in these processes bFGF and VEGF play a pivotal role.

In order to elucidate the structural requirements needed to achieve FGF and VEGF inhibitory activity, a series of porphyrin analogs was obtained or synthesized based on the slue of P1, and then examined.

The exact mechanism by which P1 and other related porphyrin like molecules inhibit growth factor-receptor binding and activation is not clear. However, our results suggest that P1 interferes with the formation of the tri-molecular complex of growth factor-heparin and the tyrosine kinase receptor (Yayon et al. 1991), thus abrogating receptor signaling. It is interesting to note that P1 does not inhibit the binding of EGF, which is not a heparin-binding or heparin dependent growth factor (Aviezer and Yayon, 1994) to its high affinity tyrosine kinase receptor, suggesting that interfering with heparin binding may play a key role in P1's inhibitory effect. Both the FGF ligand and the FGF receptor contain heparin-binding regions critical for FGF receptor activation (Schiessinger et al., 1995) and several inhibitors of FGF are direct competitors of heparin (Ornitz et al 1995, Miao et al 1997). P1 however does not resemble in its structure to any of the known heparin mimetics. Nevertheless the requirement for positively charged groups and their spatial distribution may mimic a restricted highly sulfated domain in heparin thus serving as a heparin mimetic. Several other inhibitors of FGF and VEGF which have been shown to inhibit angiogenesis were designed to inhibit the intrinsic tyrosine kinase activity of the FGF and VEGF growth factor receptors (Mohammadi et al, 1997; Fong et al, 1999). This novel class of FGF and VEGF inhibitors however, most likely works via a different molecular mechanism involving direct interference with growth factor receptor interaction, thus inhibiting their biological responses.

Porphyrin derivatives are widely used for the treatment of tumors and malignant tissues in combination with electromagnetic radiation or radioactive emissions. Since they strongly absorb light in the 690–880 nm region, many porphyrins were suggested for use as photosensitizers in photodynamic therapy (PDT) (Jori et al, 1986). Some porphyrin derivatives are used in combination with electromagnetic radiation or radioactive emissions for inhibiting angiogenesis (Margaron et al, 1996). It has been suggested that the activity of porphyrin derivatives as anti-tumor agents in the absence of electromagnetic radiation or radioactive emission may be based on their ability to cleave DNA since they must always include an excitable central Fe or Mn metal atom. Here we find that porphyrin like compounds that do not contain a metal atom, can directly interfere with growth factor receptor tyrosine kinase interactions.

The potent antiproliferative effect of P1 is of potential clinical application not only in the cancer field but also in other processes of pathological proliferation such as restenosis, accelerated atherosclerosis, and pathological angiogenesis as in diabetic retinopathy and arthritis. In support is the observation that P1 markedly inhibited the outgrowth of microvessels from aortic rings embedded in a collagen gel. Furthermore, P1 and its analogs are potent inhibitors of vascular smooth muscle cell proliferation in vitro.

The fact that it was possible, according to the present invention, to improve the potency of the P1 lead compound for its FGF and VEGF inhibitory activity, by rationally modifying specific groups on the porphyrin backbone, is of great importance. Based on the structure of P1 we have synthesized novel mesa pyridylium substituted porphyrins, in which the position of the N-methyl (the positive charge) was varied from the para-position to ortho and meta, as well as porphyrins with less than four 4-pyridylium substituents. It was then found that only cationic charged porphyrins, but not neutral or anionic charged derivatives, were active.

When meso-pyridylium substituted porphyrins, as well as porphyrins with less than four 4-pyridylium substituents, were synthesized and tested, the most beneficial effect, as judged by the inhibition of bFGF binding, was obtained with 5,10,15-tris (4-N-methylpyridylium)-20-(2,3,4,5,6-pentafluorophenyl) porphyrin triiodide (P16), a non symmetric porphyrin with three positive charges. The activity of P16 in vitro was about 50 times higher than that of P1.

Another derivative, Compound P20 (5,10,15,20-tetrakis [2,3,5,6-tetrafluoro4-(N-methyl-2-pyridylium] porphyrin tetraiodide), which contains four positive charges at more remote positions, was also significantly more active than P1. In the Lewis lung carcinoma tumor model however, only P20, but not P16, was more active than P1.

Finally, we have tested a novel water-soluble corrole analog of P1 (P21) (5,10,15-tris[2,3,5,6-tetrafluoro-4-(N-methyl-2-pyridylium]corrole triiodide) (MW 1311.3), for its activity both for in vitro inhibition of bFGF binding and for the inhibition of tumor growth. Indeed, this novel derivative showing the advantages of having three positive charges as in P16, but with the same side groups as in P20, displayed the best of both P16 and P20 characteristics, and was found to be about 10 fold more active than P1 in vitro and 5 fold more potent in the in vivo tumor models, inhibiting lung metastasis formation in vivo at a concentration of only 5 mg/kg body weight. Furthermore, P21 synthesis takes a much more straight forward approach than P16 (Gross et al, 1999).

The novel meso pyridylium-substiuted non symmetric porphyrins as well as the novel corrole-based derivatives of the invention demonstrated over 50 fold increase in activity in vitro, with significantly improved efficacy in blocking tumor progression and metastasis in vivo. The results with said novel rationally designed P1 porphyrin and corrole analogs demonstrate improved potency in inhibiting receptor binding, tumor progression and metastasis. Taken together, we have identified P1 and its analogs as a novel class of potent inhibitors of growth factors activity such as bFGF and VEGF activity in vitro and in vivo. These results suggest that rationally modified porphyrin and corrole analogs can serve as highly potent inhibitors of growth factor activity in vitro and in vivo.

The key to developing highly potent and specific anti tumor agents relies on the ability to perform chemical modifications along the course of the development process. The vast knowledge accumulated with regard to the biological and chemical properties of the porphyrins and corroles of the invention is therefore of great advantage for any potential medicinal chemistry approach This fact, along with their capacity to block growth factor mediated tumor progression and angiogenesis, make these porphyrins and corroles highly attractive candidates for the development of anticacer and other drugs.

The invention will now be illustrated by the following non-limiting Examples.

EXAMPLES

For convenience of the presentation, this section of Examples will be divided into two sections: (I) Chemical Section, with a List of the Compounds, their synthesis and characterization; and (II) Biological Section, with description of Materials, Methods and Biological Activity of the compounds.

CHEMICAL SECTION—SYNTHESIS AND CHARACTERIZATION

LIST OF COMPOUNDS

In the Examples, the following compounds P1–P21, which formulas are presented in Appendix A hereinafter just before the References, will be identified by their symbols in bold:

| | |
|---|---|
| P1 | 5,10,15,20-Tetrakis(N-methyl-4-pyridylium)-21H,23H-porphine tetra-p-tosylate |
| P2 | 5,10,15,20-Tetrakis(pentafluorophenyl)-21H,23H-porphine |
| P3 | 5,10,15,20-Tetrakis(4-methoxyphenyl)-21H,23H-porphine |
| P4 | Tetrakis(4-cumyloxyphenoxy)phthalocyanine |
| P5 | 5,10,15,20-Tetrakis[4-(trimethylammonio)phenyl]-21H,23H-porphine tetra-p-tosylate |
| P6 | 5,10,15,20-Tetrakis(N-methyl-4-pyridylium)-21H,23H-porphine aluminium hydroxide tetraiodide |

| | |
|---|---|
| P7 | 5,10,15,20-Tetrakis-(N-methyl-2-pyridylium)-21H,23H-porphine tetraiodide |
| P8 | 5,10,15,20-Tetrakis-(N-methyl-4-pyridylium)-21H,23H-porphine tetraiodide |
| P9 | 5,10,15,20-Tetrakis(N-methyl-2-pyridylium)-21H,23H-porphine tetra-p-tosylate |
| P10 | 3,8,13,18-Tetrakis(N-methyl-4-pyridylium)-21H,23H-porphine tetraiodide |
| P11 | 5,10,15,20-Tetrakis(4-carboxylatophenyl) 21H,23H-porphine tetraammonium |
| P12 | 5,10,15,20-Tetrakis(N-methyl-3-pyridylium)-21H,23H-porphine tetra-p-tosylate |
| P13 | 5,10,15,20-Tetrakis(N-methyl-3-pyridylium)-21H,23H-porphine tetraiodide |
| P15 | 5,10,15,20-Tetrakis(2,3,5,6-tetrafluoro-4-trimethyl-ammonio-phenyl)-21H,23H-methyl-porphine tetra-trifluoromethylsulfonate |
| P16 | 5-Pentafluorophenyl-10,15,20-tris(N-methyl-4-pyridylium)-21H,23H-porphine triiodide |
| P17 | 5,15-Bis(pentafluorophenyl)-10,20-bis(N-methyl-4-pyridylium)-21H,23H-porphine diiodide |
| P18 | 5,10-Bis(pentafluorophenyl)-15,20-bis(N-methyl-4-pyridylium)-21H,23H-porphine diiodide |
| p19 | 5,10,15-Tris(N-methyl-4-pyridylium)-20-(2,3,5,6-tetra-fluoro-4-aminopropyl-amino-phenyl-21H,23H-porphine triiodide |
| p20 | 5,10,15,20-Tetrakis[4-(N-methyl-2-pyridylium) 2,3,5,6-tetrafluoro-phenyl]-21H,23H-porphine tetraiodide |
| P21 | 5,10,15-Tris[2,3,5,6-tetrafluorophenyl-4-(N-methyl-2-pyridylium)]-21H,23H-corrole triiodide |

Compounds P1–P13 and P15 are known. Compounds P1, P5–P10, and P15–P21 inhibit growth factor RTK activity in at least one of the assays tested and their use is encompassed by the present invention Porphyrins P16–P20 are new and are covered by the present invention Corrole compound P21 was first disclosed in Gross, 1999 and in Israel Patent Application No. 126426 filed on 29.09.1998 by one of the coapplicants of the present application but its pharmaceutical use is herein disclosed for the first time.

[I] Example 1

Preparation of Compounds P16, P17, P18

1a) Preparation of the Intermediate Compounds—Condensation Step

A mixture of 4.3 mL (45 mmol, 3 eq.) of 4-pyridinecarboxaldehyde, 2.06 mL (16.5 mmol, 1 eq.) of pentafluorobenzaldehyde, and 4.15 mL (60 mmol, 4 eq.) pyrrole was dissolved in 300 mL of acetic acid, and the mixture was heated to reflux for 2 h After cooling to room temperature, the solvent was evaporated to dryness by vacuum and the oily residue was washed by hot water, neutralized by aqueous ammonia (25%), and washed again with hot water. The purple solids obtained by this procedure were filtered and dried. The dry solid material was treated with three portions of 50 mL of dichloromethane, each followed by filtration. To the combined organic phases, 10 g of silica were added, and the solvent was evaporated to dryness.

1b) Chromatographic Separation

Separation and purification of the components obtained in step 1a was achieved by column chromatography, in which the polarity of the eluents was gradually increased from dichloromethane to mixtures of dichloromethane and 2–10% ethanol. The order of elution (the Rf values are for silica with 2% ETOH in $CH_2Cl_2$) and the chemical yields were as follows:

5,10,15,20-tetrakis(2,3,4,5,6-pentafluorophenyl) porphyrin (1a=P2, tra, Rf=0.95).

5,10,15-tris(2,3,4,5,6-pentafluorophenyl)-20-(4-pyrdyl) porphyrin (1b, 1.1%, Rf=0.66).

5,15-bis(2,3,4,5,6-pentafluorophenyl)-10,20-bis(4-pyridyl)porphyrin (1c, Rf=0.60)*.

5,10-bis(2,3,4,5,6-pentafluorophenyl)-15,20-bis(4pyridyl)porphyrin (1d, Rf=0.54)*.

5-(2,3,4,5,6-pentafluorophenyl)-10,15,20-tris(4-pyridyl) porphyrin (1e, 9.4%, Rf=0.45). 5,10,15,20-tetrakis(4-pyridyl)porphyrin (1f, traces, Rf=0.18).

* The combined yield of compounds 1c and 1d was 13.4%. Their separation required an additional column in which the eluent was 2% ethanol in dichloromethane.

Spectroscopic characteristics of the compounds (1a and 1f are known compounds):

1a, UV-vis ($CH_2Cl_2$): $\lambda_{max}$ (nm) 412, 506, 586; $^1$H NMR ($CDCl_3$): δ8.91 (s, 8H), −2.93 (s, 2H); $^{19}$F NMR ($CDCl_3$): δ−136.9 (dd, $J_1$=22.8 Hz, $J_2$=7.0 Hz, 8F), −151.6 (t, J=20.7 Hz 4F), −161.7 (dd, $J_1$=22.4 Hz, $J_2$=5.8 Hz, 8F).

1b, UV-vis ($CH_2Cl_2$): $\lambda_{max}$ (nm) 414, 506, 582; $^1$H NMR ($CDCl_3$): δ9.06 (d, J=4.3 Hz, 2H), 8.89 (s, 6H), 8.16 (d, J=4.2 Hz, 2H), 8.15 (s, 2H), −2.92 (s, 2H); $^{19}$F NMR ($CDCl_3$): δ137.0 (m, 6F), −151.8 (m (2 overlaying t), 3F), −161.8 (m, 6F); MS$^+$ (e/z) 886.1 (MH$^+$, 100%), MS$^-$ (e/z) 884.6 (M$^-$, 40%), ([M−H]$^-$, 60%)).

1c, UV-vis ($CH_2Cl_2$): $\lambda_{max}$ (nm) 412, 508, 584; $^1$H NMR ($CDCl_3$): δ9.06 (d, J=4.4 Hz, 4H), 8.89 (s, 4H), 8.85 (s, 4H), 8.15 (d, $J_1$=4.5 Hz, 4H), −2.94 (s, 2H); $^{19}$F NMR ($CDCl_3$): δ−137.2 (dd, $J_1$=23.2 Hz, $J_2$=7.2 Hz, 4F), −152.0 (t, J=20.9 Hz, 2F), −161.9 ($J_1$=22.8 Hz, $J_2$=7.3 Hz, 4F); MS$^+$ (e/z) 797.4 (MH$^+$, 100%), MS$^-$ (e/z) 794.9 ([M−H]$^-$, 100%).

1d, UV-vis ($CH_2Cl_2$): $\lambda_{max}$ (nm) 414, 508, 582; $^1$HNMR ($CDCl_3$): δ9.06 (d, J=5.8 Hz, 4H), 8.89 (d, J=6.6 Hz, 4H), 8.84 (m, 4H), 8.15 (dd, $J_1$=4.3 Hz, $J_2$=1.5 Hz, 4H), −2.90 (s, 2H); $^{19}$F NMR ($CDCl_3$): δ−137.1 (dd, $J_1$=23.4 Hz, $J_2$=8.1 Hz, 4F), −152.0 (t, J=21.1 Hz, 2F), −161.9 (td, $J_1$=22.8 Hz, $J_2$=7.9 Hz, 4F); MS$^+$ (e/z) 797.4 (MH$^+$, 100%), MS$^-$ (e/z) 794.9 ([M−H]$^-$, 100%).

1e, UV-vis ($CH_2Cl_2$): $\lambda_{max}$ (nm) 416, 510, 586; $^1$H NMR ($CDCl_3$): δ9.05 (d, J=5.4 Hz, 6H), 8.90 (d, J=4.8 Hz, 2H), 8.84 (m (unresolved doublets), 6H), 8.14 (m (unresolved doublets), 6H), −2.92 (s, 2H); $^{19}$F NMR ($CDCl_3$): δ−137.3 (dd, $J_1$=22.8 Hz, $J_2$=7.9 Hz, 2F), −152.1 (t, J=21.7 Hz, 1F), −162.0 ($J_1$=23.0 Hz, $J_2$=7.7 Hz, 2F); MS$^+$ (e/z) 708.1 (MH$^+$, 100%), MS$^-$ (e/z) 706.1 ([M−H]$^-$, 100%).

1f, $^1$H NMR ($CDCl_3$): λ9.04 (d, J=5.5 HZ, 8H), 8.85 (s, 8H), 8.14 (d, J=5.5 Hz, 8H), −2.95 (s, 2H).

1c) Alkylation Step 70 mg (0.1 mmol) of 5-(2,3,4,5,6-pentafluorophenyl)-10,15,20-tris(4-pyridyl) porphynin (compound 1e) or any of the other derivatives 1b–1f were stirred at room temperature with 3 mL (48 mmol) $CH_3I$ in 10 mL DMF for 12 hours, after which the reaction mixture was evaporated to dryness by high vacuumn at room temperature. The resulting crystals were recrystallized from mixtures of MeOH and EtOAc, thus obtaining:

2b 5,10,15-tris(2,3,4,5,6-pentafluorophenyl)-20-(N-methyl-4-pyridylium)porphyrin iodide: UV-vis ($H_2O$): $\lambda_{max}$ (nm) 418, 516, 582.

2c (compound P17)

5,15-bis(2,3,4,5,6-pentafluorophenyl)-10,20-bis(N-methyl4-pyridylium)porphyrin diiodide: UV-vis ($H_2O$): $\lambda_{max}$ (nm) 418, 514, 580.

2d (compound P18)

5,10-bis(2,3,4,5,6-pentafluorophenyl)-15,20-bis(N-methyl-4-pyridylium)porphyrin diiodide: UV-vis ($H_2O$): $\lambda_{max}$ (nm) 416, 514, 582.

2e (compound P16)

5-(2,3,4,5,6-pentafluorophenyl)-10,15,20-tris(N-methyl-4-pyridylium)porphyrin triiodide: UV-vis (H$_2$O): $\lambda_{max}$ (nm) 420, 516, 584; $^1$H NMR (DMSO-d$_6$): δ9.48 (d, J=6.5 Hz, 6H), 9.44 (d, J=5.4 Hz, 2H), 9.17 (m, 6H), 9.02 (d, J=6.5 Hz, 4H), 8.99 (d, J=6.5 Hz, 2H), 4.71 (s, 9H), −3.13 (s, 2H); $^{19}$F NMR (DMSO-d$_6$): δ−139.3 (dd, J$_1$=24.5 Hz, J$_2$=5.8 Hz, 2H), −153.4 (t, J=22.2 Hz, 1H), −162.2 (J=23.0 Hz, J=5.1 Hz, 2H).

[I] Example 2

Preparation of 5,10,15,20-Tetrakis[4-(N-methyl-2-pyridylium) 2,3,5,6-tetrafluoro-phenyl]-21H,23H-porphine tetraiodide [P20]

2a) Preparation of the precursor 5,10,15,20-tetrakis[(4-(2-pyridyl)-2,3,5,6-tetrafluoro-phenyl)]porphyrin

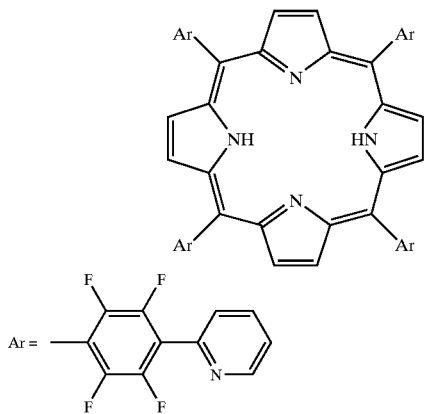

1 mL of an 1.6 M n-BuLi solution (1.6 mmol) was added to a stirred solution of 0.14 mL (1.5 mol) 2-bromopyridine in 8 mL of dry THF under an argon atmosphere at −78° C., at such a rate that the temperature of the reaction mixture did not exceed −70° C. After the addition was complete, the reaction mixture was stirred for 1 h at −78° C., resulting in a clear yellow solution. Next, a solution of 0.1 g (0.1 mmol) 5,10,15,20-tetrakis(2,3,4,5,6-pentafluorophenyl)porphyrin in 5 mL of dry THF was added dropwise. The mixture was stirred for 3 h at −78° C., and then hydrolyzed with saturated aqueous bicarbonate solution. The layers were separated, the aqueous layer washed with ether, and the combined ether extracts were dried and evaporated to a solid residue.

The product was purified by column chromatography on silica gel (2:1 EtOAc:Hexane) and recrystallized from EtOAc:EtOH to give 26–30 mg (20–25% yield) of the pure product as violet solids.

$^1$H NMR (CDCl$_3$): δ9.06 (s, 8H), 8.97 (d, J=3.9 Hz, 4H), 8.03 (t, J=7.7 Hz, 4H), 7.89 (d, J=7.5 Hz, 4H), 7.54 (t, J=6 Hz, 4H), −2.82 (s, 2H). $^{19}$F NMR (CDCl3): δ−137.57 (q, J=24.8 Hz, 8F), 144.11 (q, J=24.6 Hz, 8F). MS$^+$ (e/z) 1211.4 (MH$^+$, 100%), MS$^−$ (e/z) 1208.3 ([M−H]$^−$, 100%).

The reaction mixture gave more products (~50 mg) that eluted from the column after the desired product, with EtOAc as eluent. The main product from that mixture gave the following spectrum, indicative of more than one pyridyl ring per perfluoro ring.:

$^1$H NMR (CDCl$_3$): δ9.19 (d), 9.06 (S), 8.97(d), 8.52(d), 8.43(d), 8.0–7.0 (m), −2.79 (s). $^{19}$F NMR (CDCl3): δ−116.0 (d, 1F), −131.5 (d, 1F), −137.6(m, 8F), −144.2 (m, 8F), −145.0 (q, 1F).

2b) Alkylation Step

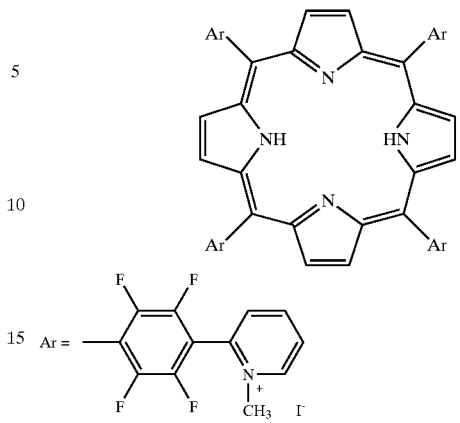

The end product P20 was obtained by alkylation of the precursor of (2a) above. Thus, a mixtre of 40 mg (33 μmol) of 5,10,15,20-tetra[4-(2-pyridyl)-2,3,5,6-tetrafluorophenyl] porphyrin of step 2a and 2.5 ml (40 mmol) of CH$_3$I in 6 mL of freshly distilled DMF was heated to 70° C. for 5 h. After evaporation of the solvent the product recrystallized from MeOH:Ether to give 55 mg (95% yield) of the title compound P20 as violet solids.

UV-vis (H$_2$O): $\lambda_{max}$ nm (ε×10$^3$) 410 (238), 508 (17.6), 574. $^1$H NMR (DMSO-d$_6$): δ9.70 (s, 4H), 9.59 (s, 4H), 9.52 (d, J=5.8 Hz, 4H), 9.04 (t, J=7.4 Hz, 4H), 8.79 (d, J=7.6 Hz, 4H), 8.54 (t, J=6.8 Hz, 4H), 4.72 (s, 12H), −3.05 (s, 2H). $^{19}$F NMR (DMSO-d$_6$)): δ−137.23 (m, 8F), 137.68 (m, 8F).

[I] Example 3

Preparation of 5-(2,2,5,6-tetrafluoro-4-N-propylamineaniline)-10,15,20-tris (N-methyl-4-pyridylium iodide) porphyrin [P19]

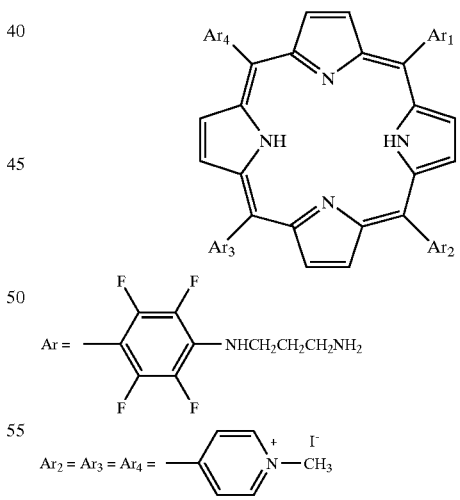

A mixture of 66 mg (58 μmol) 5-(2,3,4,5,6-pentafluorophenyl)-10,15,20-tris(N-methyl-4-pyridylium iodide)porphyrin and 0.1 mL (1.2 mmol) of 1,3-diaminopropane was dissolved in 9 mL of freshly distilled DMF and stirred overnight at room temperature. After evaporation of the solvent the product recrystallized from MeOH:Ether to give 60 mg (87% yield) of the title compound.

UV-vis (H$_2$O): $\lambda_{max}$ nm ($\epsilon \times 10^3$) 422 (176), 518 (13), 582. $^1$H NMR (DMSO6): δ9.46 (d, J=5.6 Hz, 6H), 9.14 (m, 8H), 8.99 (dd, J$_1$=12.7 Hz, J$_2$=5.8 Hz, 6H), 4.71 (s, 9H), 3.65 (d, 2H), 2.93 (t, 2H), 1.98 (t, 2H), −3.10(s, 2H). $^1$H NMR (D$_2$O): δ9.10 (d, J=5.4 Hz, 6H), 8.73 (bs, 6H), 3.59 (t, J=6.9 Hz, 2H), 3.11 (t, J=7.5 Hz, 2H), 2.05 (t, J=7.4 Hz, 2H). $^{19}$F NMR (DMSO-d$_6$): δ−142.9 (d, J=19.4 Hz, 2F), 160.5 (d, J=20.4 Hz, 2F).

[I] Example 4

Synthesis of tetrakis(N-methyl-4-pyridyl iodony) aluminium porphyrin [P6]

4a) Preparation of precursor tetrakis(4-pyridyl)porphyrin

Freshly distilled 4-pyridylaldehyde and pyrrole (1:1) were refluxed in propionic acid for 2 hrs. The solvent was removed by distillation from the reactive flask under reduced pressure. The oily black residue was washed with hot water, neutralized with aqueous NH4OH and then washed with DMF to remove the by-products. The purple precipitate was purified by means of multiple crystallization and recrystallization Yield: 12%. The product was characterized by $^1$H NMR, UV and MS.

4b) Preparation of tetrakis(4-pyridyl) aluminium porphyrin

The mixture of the product of step 4a, Al(acac)$_3$, and phenol, was heated in a pressure flask up to 230° C. for 2.5 hrs. The reactive mixture was allowed to cool to room temperature and washed with 2N NaOH and distilled water until pH neutral. Yield 78%.

4c) Preparation of aluminium tetrakis(N-methyl-4-pyridyl iodonyl) porphyrin [P6]

1 mmol solution of the product of step 4b in DMF was stirred with excess of methyl iodide at room temperature for 3 hours. The solvent was evaporated and the residue was then recrystallized twice from methanol-ether. Yield 90%.

[I] Example 5

Synthesis of tetrakis(N-methyl-2-pyridyl iodonyl) porphyrin [P7]

a) Preparation of 5,10,15,20-tetrakis(2-pyridyl)porphyrin

The procedure is the same as described in Example 4a above for the 4-pyridyl compound but the purification and isolation procedures are different. Unlike the 4-analogue, this porphyrin dissolves in DMF, so the isolation and purification have been done through the use of column chromatography on Floricil for initial isolation of the target product from black precipitate and then with use of Silica Gel column for purification of the compound. The further crystallization and multiple recrystallization led to the pure target product.

5b) Preparation of zinc tetrakis(2-pyridyl)porphyrin

To the refluxing mixture of the product of step 5a in DMF, acetate salt of zinc was added and the mixture was stirred for an additional 15 min. Then the flask was cooled and the purple precipitate was washed with methanol and ether. Yield 90%. This Zn-porphyrin was prepared in order to protect the core N—$\underline{H}$ atoms from possible methylation.

5c) Methylation

Methylation of the product of step 5b was performed as described for the 4-analogue in Example 4c with methyl iodide. Methylation of the Zn-porphyrin was done as with free-base porphyrin. The NMR shows that core N—$\underline{H}$ doesn't undergo any methylation in the free base compound.

5d) Deprotection from Zn

Deprotection from Zn was done by extraction with 1% HCL. The product obtained after deprotection contains 9% of unrecognized compound. No purification was done because the target product was already obtained by direct methylation of the free-base porphyrin.

The non-charged intermediate of step 5a and the end product P7 were characterized as follows: 5,10,15,20-tetrakis(2-pyridyl)porphyrin: UV-vis (CH$_2$Cl$_2$): $\lambda_{max}$ (nm) 416, 512, 588; $^1$H NMR (CDCl$_3$): δ9.13 (m, 4H), 8.85 (s, 8H), 8.18 (m, 4H), 8.11 (m, 4H), 7.70 (m, 4H), −2.84 (s, 2H). P7: UV-vis (H$_2$O): $\lambda_{max}$ (nm) 414 (log $\epsilon$=5.03), 510, 580.

[I] Example 6

Synthesis of tetrakis(N-methyl-4-pyridyl iodonyl) porphyrin [P8]

The title compound was prepared by methylation with excess of methyl iodide from the free base parent porphyrin and purified by crystallization.

[I] Example 7

Synthesis of tetrakis(N-methyl-4-pyridyl tosyl) porphyrin [P1]

The title compound, as the p-tolucnosulfonato salt, was prepared by methylation with excess of methyl p-toluene sulfonate from the free base parent porphyrin by reflux in DMF and purified by crystallization.

[I] Example 8

Synthesis of tetrakis(N-methyl-2-pyridyl tosyl) porphyrin [P9]

The title compound was prepared by methylation with excess of methyl p-toluene sulfonate from the free base parent porphyrin by reflux in acetone and purified by crystallization.

[I] Example 9

Synthesis of tetrakis(4-carboxyl) porphyrin ammonium salt [P11]

A mixture of freshly distilled pyrrole and p-carboxyl-benzaldehyde were refluxed in propionic acid for 3 hrs. The precipitated purple crystals were obtained after cooling the mixture, and then it was filtered. The obtained product was of 95 % purity. In order to obtain a more pure product the porphyrin was treated by NaHCO$_3$ and extracted with ethyl acetate and methylene chloride. The organic impurities were transferred into the organic layer whereas the target product as the Na salt was in aq. layer. The further neutralization with HCl to pH<6 led to the formation of crystal acidic porphyrin which was filtered and dried. The green crystals then were treated by 2M ammonia in methanolic solution until the green color changed to the purple one. The title product was crystallized with water-methanol-methylene chloride. Yield 23%.

[I] Example 10

Synthesis of Compounds P12 and P13

Compounds P12 and P13 are known and were prepared by alkylation with methyl iodide (P13) or methyl toluene sulfonate (P12) of the known non-charged intermediate: 5,10,15,20-tetrakis(3-pyridyl)porphyrin [Chemical Abstract Registry No: 40882-83-5]: $^1$H NMR (CDCl$_3$): δ9.45 (s, 4H), 9.06 (d, J=5.5 Hz, 4H), 8.85 (s, 8H), 8.52 (d, J=7.8 Hz, 4H), 7.77 (dd, J$_1$=7.8 Hz, J$_2$=5 Hz, 4H), −2.86 (s, 2H). P13

5,10,15,20-tetrakis(N-methyl-3-pyridylium) porphyrin tetraiodide: UV-vis (H$_2$O): $\lambda_{max}$ (nm) 416, 514, 582.

[I] Example 11

Preparation of 5,10,15-tris[4-(N-methyl-2-pyridylium iodide)-2,3,5,6-tetrafluoro phenyl] corrole [P21]

11a) Preparation of intermediate 5,10,15-tris(4-(2-pyridyl)-tetrafluorophenyl) corrole.

0.42 mL of an 1.6 M n-BuLi solution (0.7 mmol) was added to a stirred solution of 0.054 mL (0.56 mmol) 2-bromopyridine in 6 mL of dry THF under an argon atmosphere at −78° C., at such a rate that the temperature of the mixture did not exceed −70° C. After the addition was complete, the reaction mixture was stirred for 1 h at −78° C., to give a clear yellow solution. Next, a solution of 0.03 g (0.038 mmol) 5,10,15-tri(2,3,4,5,6-pentafluorophenyl) corrole in 6 mL of dry THF was added dropwise. The mixture was stirred for 1 h at −78° C. and then hydrolyzed with saturated aqueous bicarbonate solution. The layers were separated, the aqueous layer washed with ether, and the combined ether extracts were dried and evaporated to a solid residue.

The product was purified by column chromatography on silica gel (1:1 EtOAc:Hexane) and recrystallized from CH$_2$Cl$_2$: hexane to give 13 mg (35% yield) of the pure product as violet crystals.

UV-vis (CH$_2$Cl$_2$): $\lambda_{max}$ nm414 (111.6), 564 (18.4), 606. $^1$H NMR (CDCl$_3$): 9.12 (d, J=3.9 Hz, 2H), 8.93 (m, 5H), 8.73 (d, J=4.88 Hz, 2H), 8.66 (d, J=3.91 Hz, 2H), 8.00 (dt, J$^1$=7.81 Hz, J$^2$=1.95 Hz, 3H), 7.84 (bd, J=7.81 Hz, 3H), 7.51 (dt, J$^1$=6.84 Hz, J$^2$=1.95 Hz, 3H), −2.02 (bs, 3H). $^{19}$F NMR (CDCl$_3$): −138.19 (q, J=23.79 Hz, 2F), −138.81 (q, J=23.79 Hz, 4F), −144.11 (q, J=23.79 Hz, 4F), −144.57 (q, J=23.79 Hz, 2F). MS$^+$ (e/z) 972.9 (MH$^+$, 100%), MS$^−$ (e/z)972.7 ([M−H]$^−$, 100%).

11b) Preparation of title Compound P21

A mixture of 11 mg (11 μmol) of 5,10,15-tri(4-(2-pyridyl)-2,3,5,6-tetrafluoro phenyl)corrole prepared in step 11a and 0.8 mL(13 mmol) of CH$_3$I in 2 mL of freshly distilled DMF was heated to 70° C. for 3 h. After evaporation of the solvent the product was recrystallized from MeOH:Ether to give 15.5 mg (98% yield) of the title compound as green solids.

UV-vis (MeOH): $\lambda_{max}$ nm (ε×10$^3$) 430 (76.2), 576 (10.9), 622 (17.8). $^1$H NMR (DMSO-d6): 9.49 (d, J=5.98 Hz, 3H), 9.16 (bm, 8H), 9.00 (t, J=8.54 Hz, 3H), 8.75 (t, J=7.68 Hz, 3), 8.51 (t, J=7.68 Hz, 3H), 4.68 (s, 3H), 4.65 (s, 6H). $^{19}$F NMR (DMSO-d6)): d−137.26(bm, 4F), −138.04 (bm, 6F), −138.60 (bm, 2F).

II BIOLOGICAL SECTION

MATERIALS

Human recombinant bFGF was from American Cyanamid (Pearl River, N.Y.); heparin-coated plates were from Carmeda (Sweden); FRAP was prepared as described (Ornitz et al, 1992); NIH 3T3 cells expressing signal peptide bFGF were generated as described (Yayon and Klagsbrun, 1990); anti-FGFR3 antibody and anti-phosphotyrosine antibody PY-20 were purchased from Santa Cruz Biotechnology (Santa Cruz, Calif.); anti-ERK 1,2 antibody was purchased from Sigma; DMEM was from Bet Haemek Biological Industries (Israel); compounds P1, P2, P3, P4, P5 were either synthesized or purchased from Aldrich (catalog Nos 32,349-7, 25,292-1, 25,288-3, 41,2066, 30,678-9, respectively); human recombinant VEGF was generated by H. Weich, Braunschwig (Germany); anti-AP antibodies were prepared as previously described (Ornitz et al, 1992).

Methods (i) Animals and Treatment Male Balb/C nude and C57/black mice were maintained on lab chow and tap water and were housed with a 12-h day-night cycle.

(ii) Binding of soluble FGFR-1 alkaline phosphatase fusion protein (FRAP) to immobilized bFGF. A high throughput screening system composed of a heparin matrix, bFGF and FGFR-1 tagged by alkaline phosphatase (FRAP), was designed using 96-well plates to which heparin has been covalently attached. bFGF was then bound to immobilized heparin, followed by the addition of FRAP and the compounds to be screened for testing their ability to modulate heparin-FGF, receptor-heparin and receptor-FGF interactions. The end-point of the assay measured enzymatically the formation of FGF-receptor complexes quantitated by the specifically associated alkaline phosphatase (AP) catalyzed chromogenic product. Thus, a lowered or elevated AP value, relative to a control, indicates modulation of binding at one or more of the three levels of interactions required for the formation of the FGF-FGFR-heparin tern complex (a lowered AP activity indicates inhibition). bFGF (100 ng/ml) was incubated on 96-well plates to which heparin has been covalently attached (Carmeda, Sweden).

Subsequently, 200 μl of FRAP condition medium and porphyrin/corrole compound were added and incubated together for 2 h. After three cycles of washing with HNTG (20 mM Hepes pH 7.5, 150 mM NaCl, 1% Triton X-100 and 10% glycerol), alkaline phosphatase substrate (Sigma) (15 mM) was added and catalyzation of the chromogenic product was measured by spectrophotometry at 405 nm.

(iii) Binding of $^{125}$I-bFGF or $^{125}$I-FGF9 to s luble FGFR-1 or FGFR-3. Conditioned medium from NIH 3T3 cells secreting soluble FRAP or FGFR-3 FR-3-AP, was incubated for 45 min at room temperature with rabbit anti-human placental AP antibodies (generated as described in Ornitz et al, 1991) prebound to agarose-protein A beads Pierce). The FGFR-1 or FGFR-3-coupled beads were washed three times with 1 ml HNTG and incubated with 2 ng/ml of $^{125}$I-FGF, 1 μg/ml of heparin and porphyrin/corrole compound at different concentrations for 1 h at room temperature. High affinity-bound $^{125}$I-bFGF was determined by counting of the samples in a γ-counter.

(iv) Binding of $^{125}$I-bFGF and $^{125}$I-FGF9 to cells. Confluent cultures of CHO cells expressing FGFR-1(Yayon et al, 1991) or FGFR-3 (Hecht et al, 1995) in 24-well plates (Falcon) were precooled and washed twice with cold DMEM supplemented with 20 mM Hepes (pH 7.5) and 0.1% bovine serum albumin (DMEM/BSA). They were then incubated for 1.5 h at 4° C. with $^{125}$I-bFGF (2 ng/ml) and increasing concentrations of porphyrin/corrole compound. The binding medium was discarded and the cells were washed once with ice-cold DMEM/BSA and twice with cold PBS (pH 7.5) containing 1.6M NaCl. High-affinity receptor-bound bFGF was determined by extraction of the cells with 20 mM Na acetate pH 4.0 containing 2.0 M NaCl. Non-specific binding was determined in the presence of a 100-fold excess of unlabeled bFGF.

(v) Inhibition by porphyrins of tumor formation induced by signal peptide bFGF expressing cells NIH 3T3 cells expressing signal peptide bFGF were injected subcutaneously to Balb/C nude mice as described (Yayon and Klagsbrun, 1990). Porphyrin/corrole compound at 25 μg/g of body mass was injected IP (intraperitoneally) twice a week and after 4 weeks the tumor size was measured.

(vi) Rat aorta in vitro angiogenesis assay. Rings of rat aorta sections were immobilized in a three-dimensional collagen gel, in the presence of serum free growth medium (D/MEM)

(Nicosia & Ottinetti, 1990). Porphyrin or corrole compound and bFGF (2 ng/ml) were added to the growth medium twice a week when indicated. After 14 days the cultures were fixed, and the extent of microvascular endothelial tube outgrowth was measured under a light microscope (Miao et al., 1997).

(vii) Lewis lung carcinoma tumor assay. Murine Lewis lung carcinoma (LLC) D122 cells ($1 \times 10^6$ cells/50 ml PBS) were injected into the foot pads of 10-week old C57 black mice (O'Reilly et al, 1994). Twenty five µg/g of body mass of porphyrin or corrole compound dissolved in PBS were injected IP twice a week to the treated group, and tumor size was measured periodically in order to follow primary tumor formation. In order to evaluate inhibition of lung metastasis by porphyrin or corrole compound, the primary tumors were allowed to develop over a period of six weeks to a volume of approximately 8 $mm^3$; after which the tumors were removed and metastases were allowed to develop for four weeks. During this time the treated group received 25 µg/g of body mass of porphyrin or corrole compound IP twice a week. Subsequently the mice were sacrificed, dissected and the lungs removed and photographed. The extent of lung metastasis was measured by weighing the lungs.

(viii) Immunoblots. To the overnight serum-starved cells (2 plates for each treatment), 500 µl of $F12^{++}$ medium were added which either contained or not the respective porphyrin or corrole compound in a final concentration of 1 µ/ml for 40 min at 37° C. One of the two plates of each treatment was then stimulated with FGF9 (+) (75 ng/ml) and to the second plate only medium (−) was added for 10 min at 37° C. The cells were washed twice with PBS. 600 µl of SBN lysis buffer containing 1% NP-40 and 1 mM vanadate were added and left on ice for 10 min. The plates were then scraped and left on ice for additional 10 min. The lysate was span down in Eppendorf centrifuge for 15 min, 15000 rpm at 4° C. The supernatants were kept and Bradford protein determinant on assay was performed in the samples. 500 µg protein from each sample were taken for immunoprecipitation with 7.5 µl antibody against FGFR-3, 4 hr at 4° C. The immunoprecipitated samples as well as total lysates (40 µg) were separated on 7.5% polyacrylamide SDS-PAGE and then transferred to nitrocellulose paper and immunoblotted with the subsequent antibodies.

ix) Binding of soluble VEGF receptor alkaline phosphatase fusion protein to immobilized VEGF. The flt-1 VEGF receptor was expressed as a fusion protein with AP as previously described (Roeckl et al, 1998) and tested for its binding capacity to immobilized VEGF as described in method (ii) above for the FGF receptor.

x) Binding of $^{125}$I-VEGF to cells. Confluent cultures of bovine aortic endothelial cells transfected with the VEGF receptor KDR were tested for binding of radiolabeled $^{125}$I-VEGF as described in method (iv) above for the FGFR-1 expressing cells.

[II] Example 1

Compound P1 Inhibits Binding of bFGF to FGFR-1 in Vitro

In order to identify inhibitors of FGF-FGFR interactions, an assay for testing FGFR-ligand binding was developed. The system is composed of bFGF bound to a heparin matrix to which soluble FGFR-1 ectodomain alkaline phosphatase fusion protein (FRAP) and the screened compounds are added (see Methods, section (ii)). The screening according to the invention identified several compounds for their capacity to inhibit soluble FGF receptor (FRAP) binding to FGF immobilized on heparin, the first and very potent one being Compound P1.

For evaluation of the capacity of P1 to inhibit bFGF-induced activity, its ability to inhibit bFGF binding to FGFR-1 was first tested in in vitro systems. P1 was tested for its capacity to inhibit binding of FRAP to bFGF immobilized on heparin matrix. As shown in FIG. 1A, P1 demonstrated potent inhibition at $IC_{50}$ of 90 ng/ml, with a distinct dose-dependent inhibition pattern.

Figure 1B:
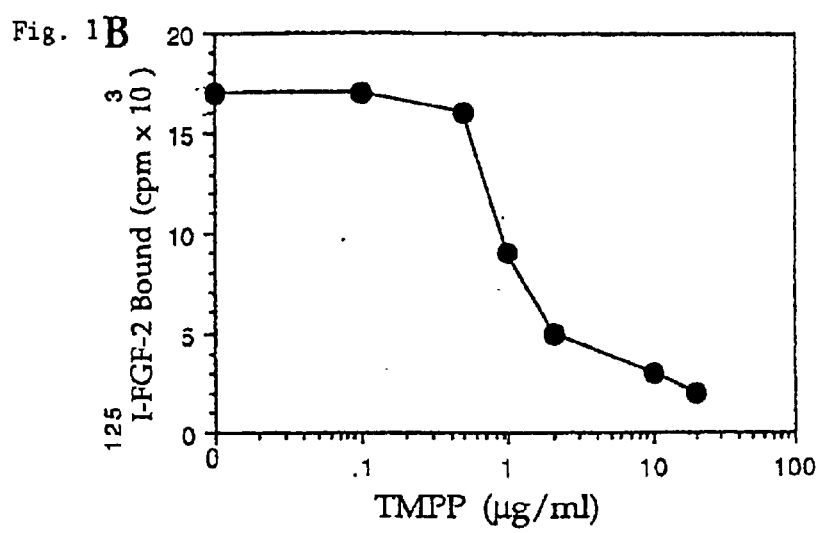
Figure 1C:
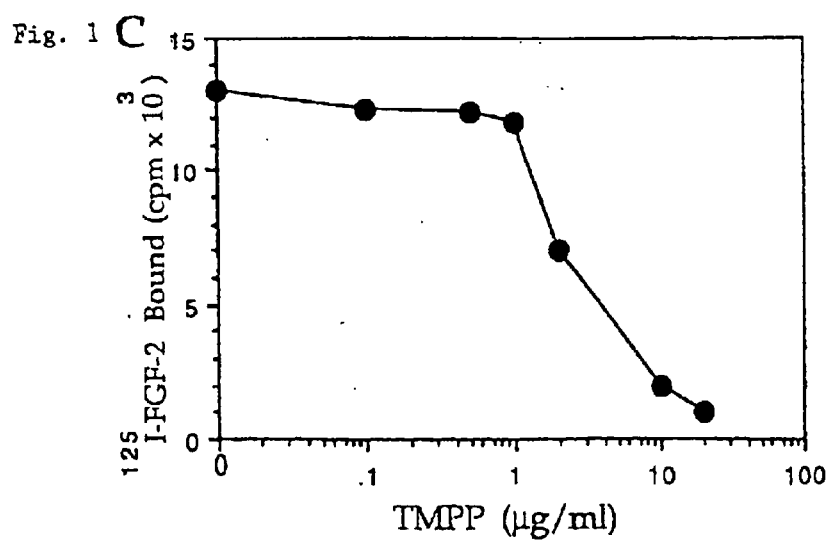

In order to further examine the capacity of P1 to inhibit bFGF receptor binding, we measured the binding of radio-labeled $^{125}$I-bFGF to FGFR in two experimental systems. First we utilized a cell-free system, measuring the binding of radiolabeled bFGF to a dimeric soluble FGFR-1 fused to alkaline phosphatase. The soluble FRAP was immobilized using an anti-alkaline phosphatase antibody prebound to agarose-protein A beads (see Methods, section (iii)). As a second experimental model, we used CHO cells deficient in heparan sulfate and genetically engineered to express FGFR-1 (Methods, section (iv)). P1 inhibited binding of $^{125}$I-bFGF to the FGF receptor in both experimental systems. FIG. 1B illustrates that the porphyrin P1 is capable of profoundly inhibiting bFGF-FGFR1 binding in the soluble receptor (FRAP) assay in a dose dependent manner with an $IC_{50}$ of about 1 µM. In the cellular receptor system, P1 was capable of inhibiting bFGF binding with an $IC_{50}$ of approximately 2.5 µM (FIG. 1C). The slightly higher concentrations of P1 required for inhibition of cellular bFGF binding in the cellular assay may result from the reduced affinity of the soluble FGFR to the FGF ligand (Ornitz et al, 1992).

[II] Example 2

Inhibition of Covalent Cross-linking of $^{125}$I-bFGF and $^{125}$I-FGF9 to CHO Cells by Compound P1

Figure 2:
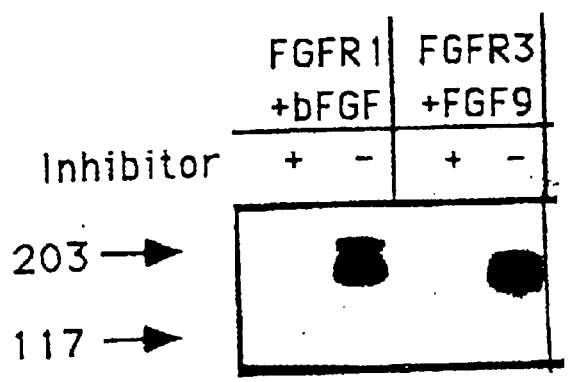
FIG. 2 shows the inhibitory effect of P1 on the covalent cross-linking of $^{125}$I-FGF and $^{125}$I-FGF9 to CHO cells transfected with FGFR-1 and FGFR-3, respectively. Binding of $^{125}$I-bFGF to confluent monolayers of PGFR-1 expressing CHO cells or $^{125}$I-FGF9 to FGFR-3 expressing CHO cells, was performed as described in Methods, section (iv), in the presence or absence of P1 (Inhibitor). After 90 min, disuccinylimidyl suberate [DSS] (0.15 mM in PBS) was added and the protein complexes were separated by electrophoresis on a 7.5% SDS-polyacrylamide gel, and analyzed by autoradiography.

In order to unequivocally determine the specificity of the binding inhibition, chemical cross-linking of $^{125}$I-bFGF and $^{125}$I-FGF9 to CHO cells transfected with FGFR-1 and FGFR-3, respectively, was carried out as described in Methods, section (iv), in the absence or presence of increasing concentrations of P1. As shown in FIG. 2, P1 can inhibit bFGF receptor binding as demonstrated by the inhibition of formation of a typical bFGF-receptor complex, in agreement with the direct binding data shown in FIG. 1C. Suramin, a well known tyrosine kinase inhibitor, served as a positive control and demonstrated FGF receptor binding inhibition. These results support the notion that the presence of P1 inhibits the binding of bFGF to the high affinity FGF tyrosine kinase receptors.

[II] Example 3

Inhibition of In Vitro Angiogenesis by Compound P1

Figure 3:
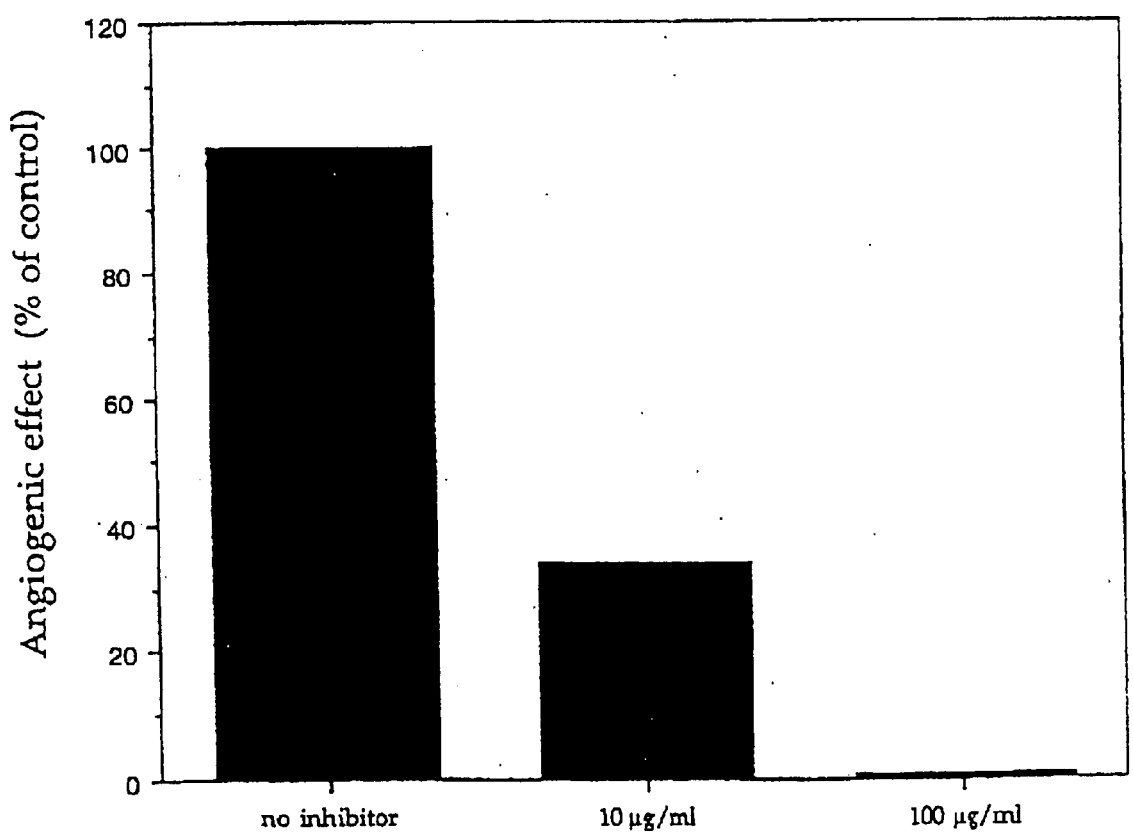
FIG. 3 illustrates an in vitro angiogenic assay using a rat aorta section immobilized in a collagen gel. Sections of rat aorta were immobilized in a collagen gel and the extent of endothelial cell growth and microvascular tubules sprouting from the vessel tissue embedded in the gel was measured upon the addition of bFGF to the medium, in the absence (no inhibitor) or presence of 10 and 100 µg/ml of P1. The results are expressed as the percent of microvascular tubule sprouting in comparison to the control experiment of bFGF addition. Basal tubule formation could be detected even when no additional factors were added.

The effect of P1 was further examined in a biological assay for angiogenesis in vitro. Angiogenic vascularization is a process in which bFGF is known to play a pivotal role (Folkman, 1989). To examine the inhibitory effects of the porphyrin on bFGF-promoted angiogenesis, we employed an in vitro angiogenic assay using rat aorta sections embedded in a collagen gel (Methods, section (vi)). The assay measures the extent of endothelial cell growth and microvascular tubules sprouting from the vessel tissue embedded in the gel. Basal tubule formation can be detected even when no additional factors are added. As shown in FIG. 3, the addition of 2 ng/ml bFGF alone dramatically increased the degree of cell growth and vascularization, however the addition of 2 ng/ml bFGF combined with P1 at concentrations of 10 μM dramatically reduced the extent of endothelial cell growth as compared to the bFGF control. When 100 μl P1 was added in the presence of 2 ng/ml bFGF, complete inhibition of microvascular tubules was achieved and no endothelial cell growth was observed.

[II] Example 4

Tumor Formation Induced by Signal Peptide bFGF Expressing Cells is Inhibited by Compound P1

Figure 4:
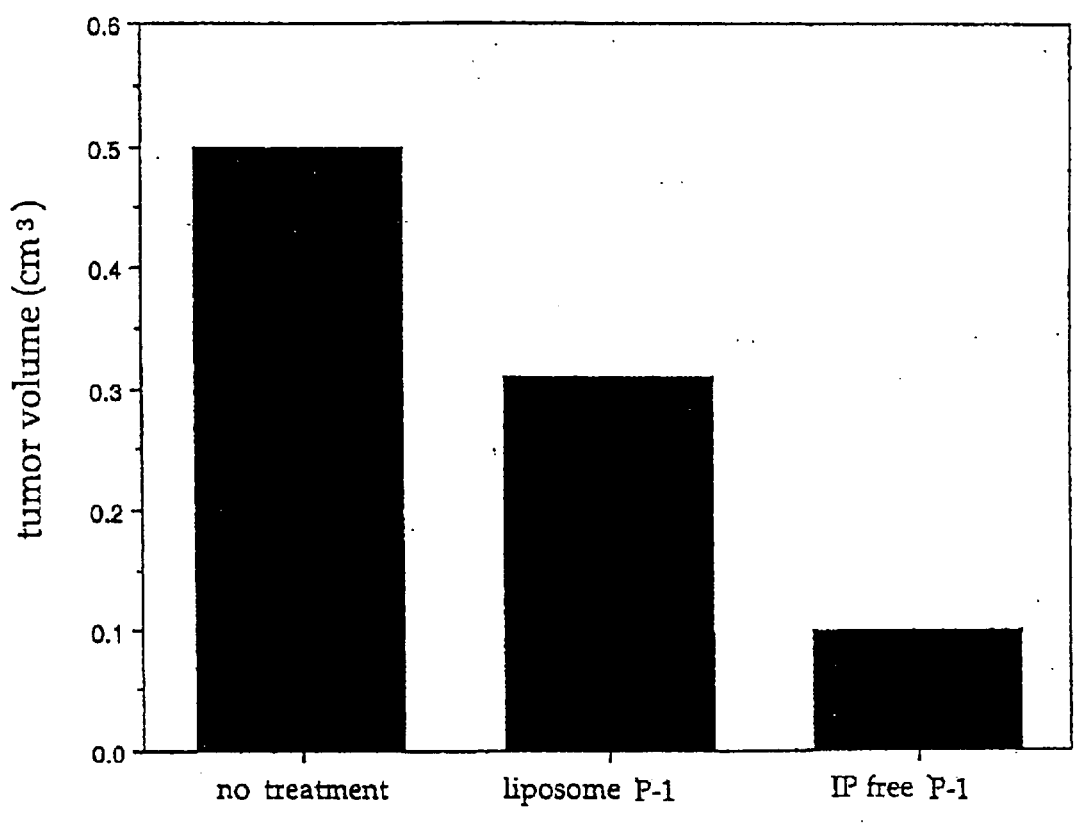
FIG. 4 shows the inhibitory effect of P1 on tumor growth induced by signal peptide bFGF in a nude mice model. NIH 3T3 cells expressing signal peptide bFGF were injected subcutaneously to Balb/C nude mice. Twenty five µg/g of body mass of free or liposome incorporated P1 were injected intraperitoneally (IP) twice a week. Tumor size was measured after 4 weeks.

After establishing the ability of P1 to inhibit FGF biological activity in vitro, the capacity of P1 to inhibit bFGF-induced tumor growth and metastasis was evaluated in vivo. First, the inhibition of tumor growth induced by signal peptide bFGF in a nude mice model was measured (Methods, section (v)). Upon addition of a signal peptide residue to bFGF, the protein is capable of transforming NIH 3T3 cells which, when injected to nude mice, grow and form a tumor Rayon & Klagsbrun, 1990). NIH 3T3 cells expressing signal peptide bFGF were injected subcutaneously to Balb/C nude mice, and P1 either free or liposome incorporated (as described by Jori and Reddi, 1993) (25 μg/g of body mass) were given twice a week by intraperitoneal injection. After 4 weeks, a clear inhibition of tumor formation by the free P1 could be seen (FIG. 4). These results indicated that P1's capacity to inhibit bFGF receptor binding was not limited to in vitro interactions alone but could be shown in in vivo assays as well.

[II] Example 5

Figure 5:
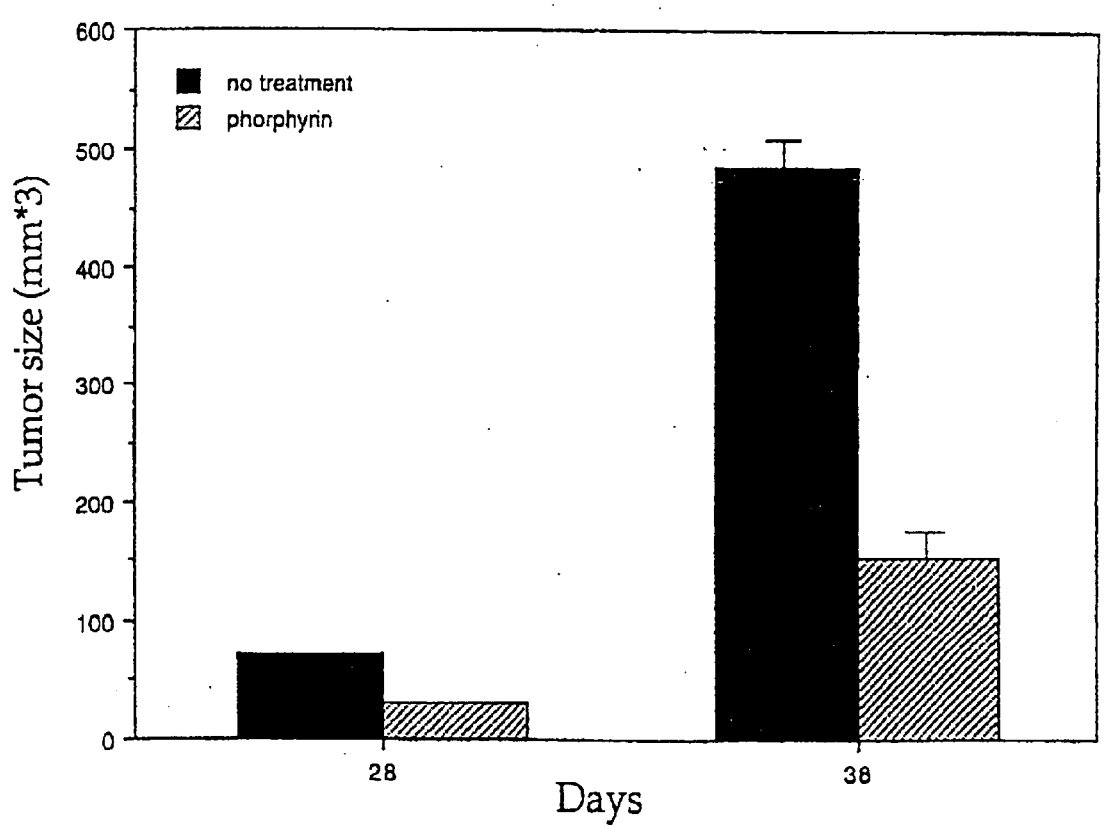
FIG. 5 shows inhibition of primary tumor growth in the Lewis lung carcinoma (LLC) murine tumor model by porphyrin P1. Lewis lung carcinoma cells were injected into the foot pads of 10-week old C57 black mice. Twenty five μg/g of body mass P1 were injected intraperitoneally twice a week and tumor size was measured after 4 weeks.

Compound P1 Inhibits the Appearance of Primary Tumors in the Lewis Lung Carcinoma (LCC) Tumor Model Inhibition of primary tumor growth was tested using the well-established LLC murine tumor growth and metastasis model (Methods, section (vii)). LLC D122 cells (200,000 cells per mouse) were injected into the foot pads of 10-week old C57 black mice. Mice having received Compound P1 (25 μg/g of body mass) by intraperitoneal (IP) injections twice a week, as described in Methods, section (vii), for 5 weeks, showed a marked inhibition in primary tumor growth in comparison to the control group (FIG. 5). The inhibition of the foot pad primary carcinoma tumor growth was statistically established and reproducible in five experiments. These results indicate that P1 is not only active in vitro, but it is capable of inhibiting tumor growth in vivo as well.

[II] Example 6

Compound P1 Inhibits Lung Metastasis in the Lewis Lung Carcinoma Model

Figure 6:
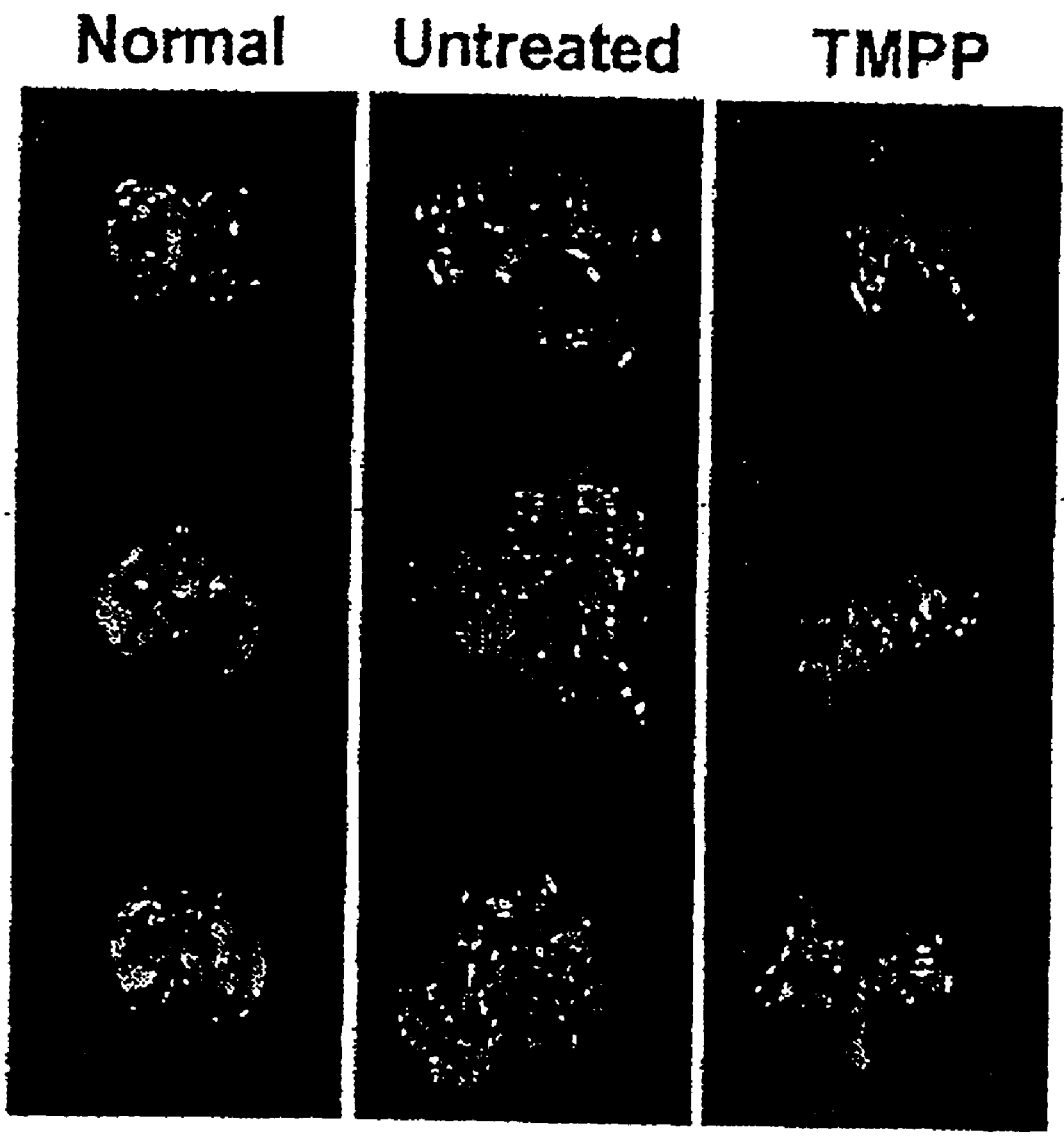
FIG. 6 shows inhibition of metastasis growth in the LLC murine tumor model by P1. Lewis lung carcinoma cells were injected into the foot pads of C57 black mice and primary tumors were allowed to develop. After their formation, the primary tumors were removed and metastases were allowed to develop for four weeks before mice were sacrificed. Twenty five μg/g of body mass P1 were injected intraperitoneally twice a week. The mice were sacrificed, dissected and the lungs removed and photographed.
Figure 7:
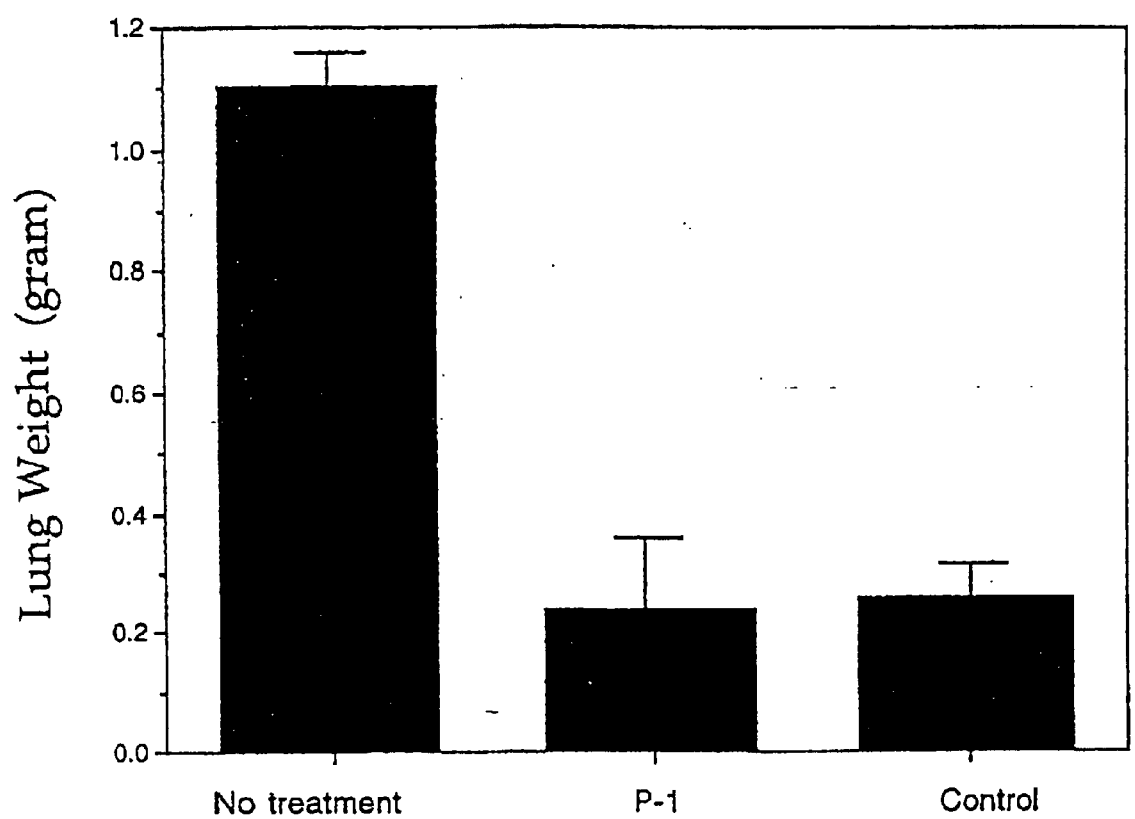
FIG. 7 depicts quantitative analysis of the inhibition of metastasis growth in the LLC murine tumor model by P1. Murine lung metastases were induced as described in Methods, section (vii). The mice were sacrificed and the extent of lung metastasis was measured by weighing the lungs.

After establishing the capacity of P1 to inhibit primary tumor growth, the capacity of P1 to inhibit lung metastasis formation was measured as described in Methods, section (vi). Mice were injected with LLC cells (200,000 cells per mouse) into the foot pad and primary tumors were allowed to develop over a period of 3 to 4 weeks to a volume of approximately 8 mm³. Subsequently, primary tumors were removed through amputation and lung metasases were allowed to develop for four weeks before the mice were sacrificed. The extent of lung metastasis at this point was examined by gross morphological examination and by determining the gain in lung weight. FIG. 6 shows that, as expected, aggressive metasis formation occurred in the non-treated mice, while in the mice that were treated with Compound P1 (25 μg/g of body mass), the lungs were similar to the control mice, with no metastatic phenotype (FIG. 6). In order to quantitate the results from these experiments, the lungs from all mice were weighed and evaluated for the extent of metastatic growth. As can be seen in FIG. 7, the control lungs from mice who were not injected with tumor cells weighed around 200 mg as do the lungs from mice treated with P1.

[II] Example 7

Inhibitory Effects of Porphyrins and Corroles on the Binding of bFGF to FGFR-1 In Vitro Porphyrin compounds P2–P20 and corrole compound P21 were tested as described in Example 1, according to Methods, sections (ii) and (iii). The results are shown in Table 1 and in FIGS. 8A–8B.

Figure 8A:
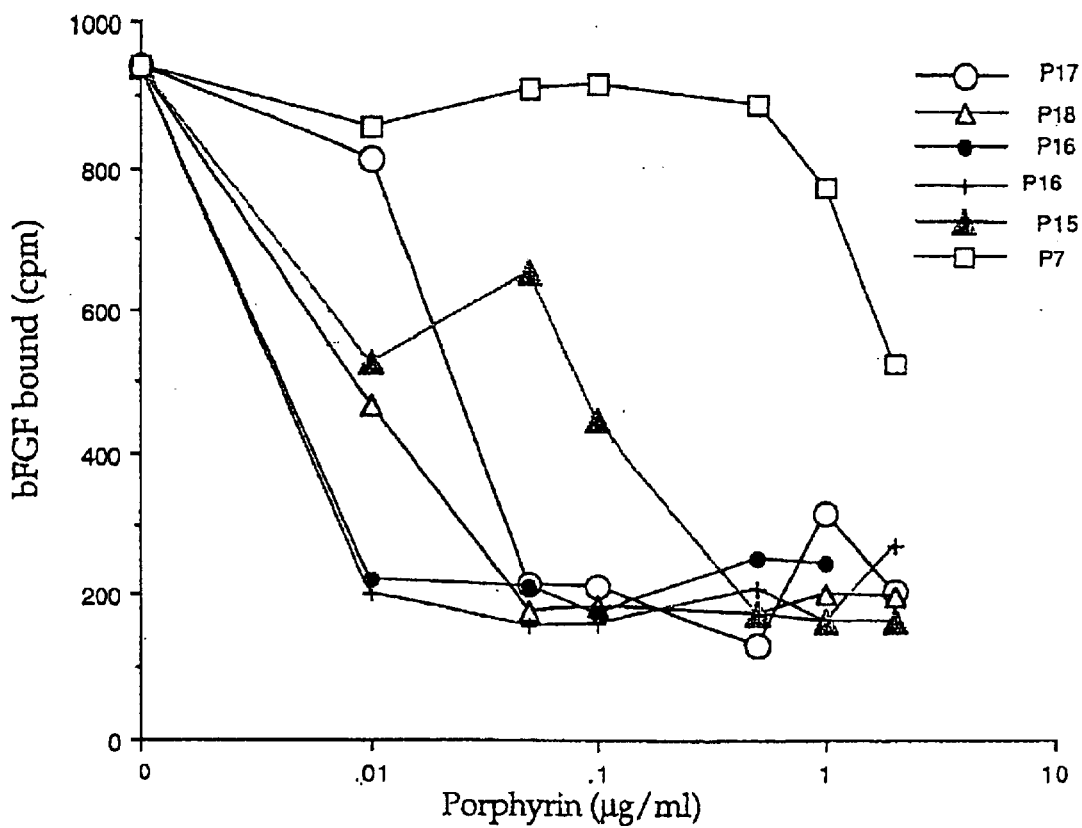
Figure 8B:
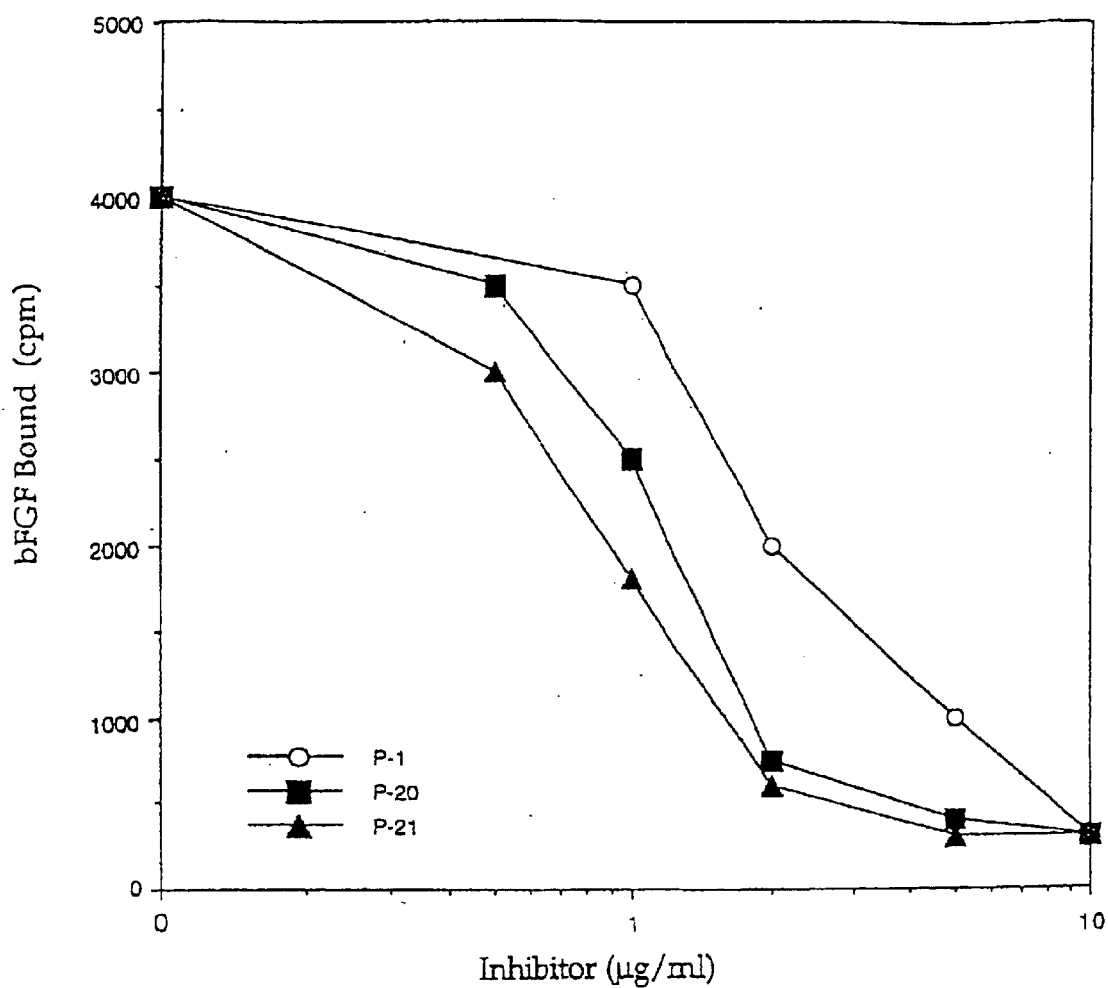

As can be seen in FIG. 8A, compounds P15 to P18 were active in vitro when tested for inhibition of FRAP binding to immobilized bFGF. The next round of porphyrins were tested for their capacity to inhibit radiolabeled bFGF binding to immobilized receptor. As shown in FIG. 8B, P16 and P18 inhibited the binding of bFGF with an activity over 100 fold higher than that of P1, indicating that they might have a high potential as bFGF inhibitors.

[II] Example 8

Inhibitory Effects of Porphyrins and Corroles In Vivo in the LLC Tumor M del

Figure 9:
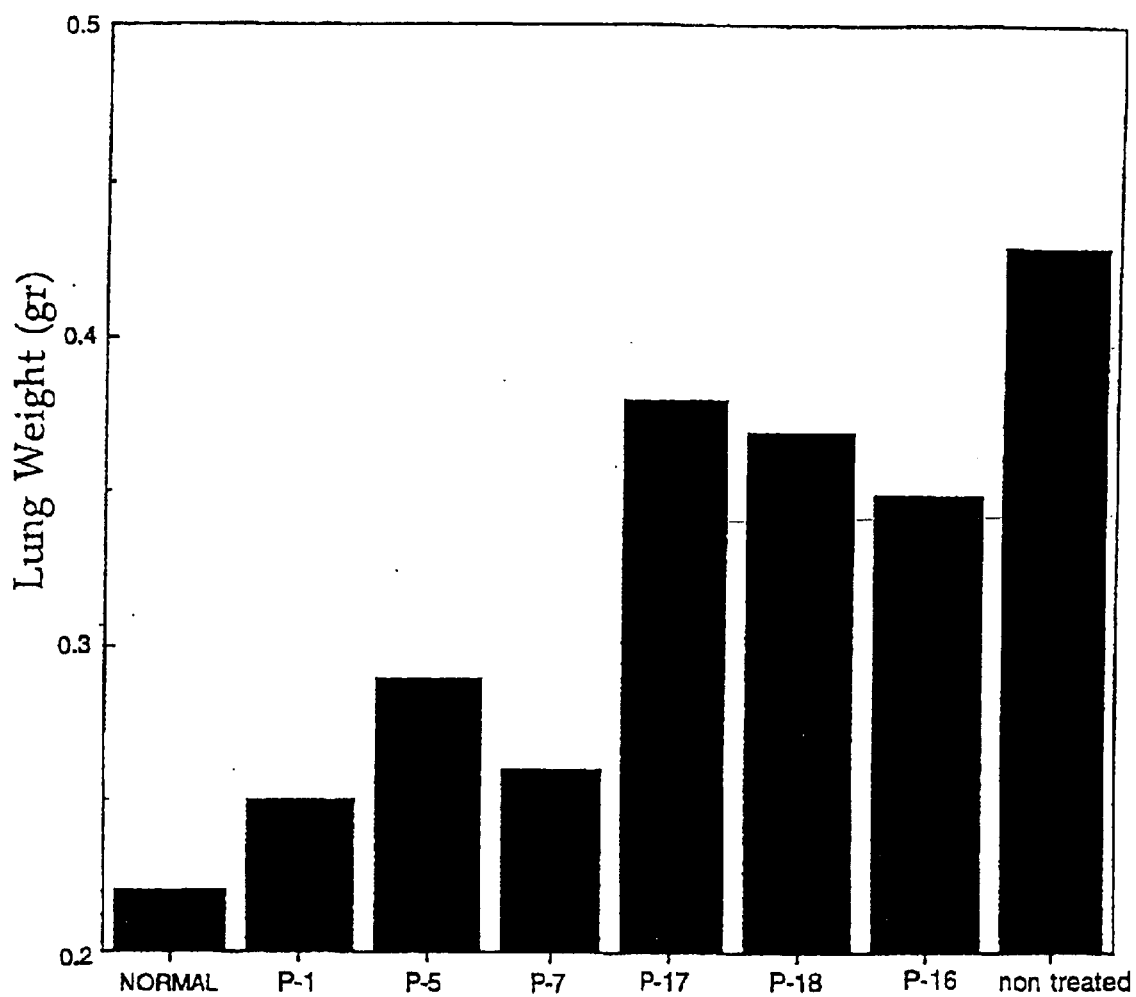
FIG. 9 shows quantitative analysis of the inhibition of metastasis growth in the LLC tumor model by various porphyrins. The experiment was conducted as described in FIG. 7.

Compounds P1–P21 were tested for capacity to inhibit the appearance of lung metastasis in the LLC model, as described in Example 6. The results are shown in Table 2 and in FIG. 9. Compounds P16–P18 were not as potent as the lead Compound P1 while P5 and P7 had a similar activity as P1 (FIG. 9). Compounds P20 and P21, shown in Example 7 (FIG. 8B) to inhibit bFGF binding in vitro, were also shown here to be highly active in vivo in the LLC tumor model (Table 2).

[II] Example 9

Compound P1 Inhibits the Binding of VEGF to VEGF-R

Figure 10A:
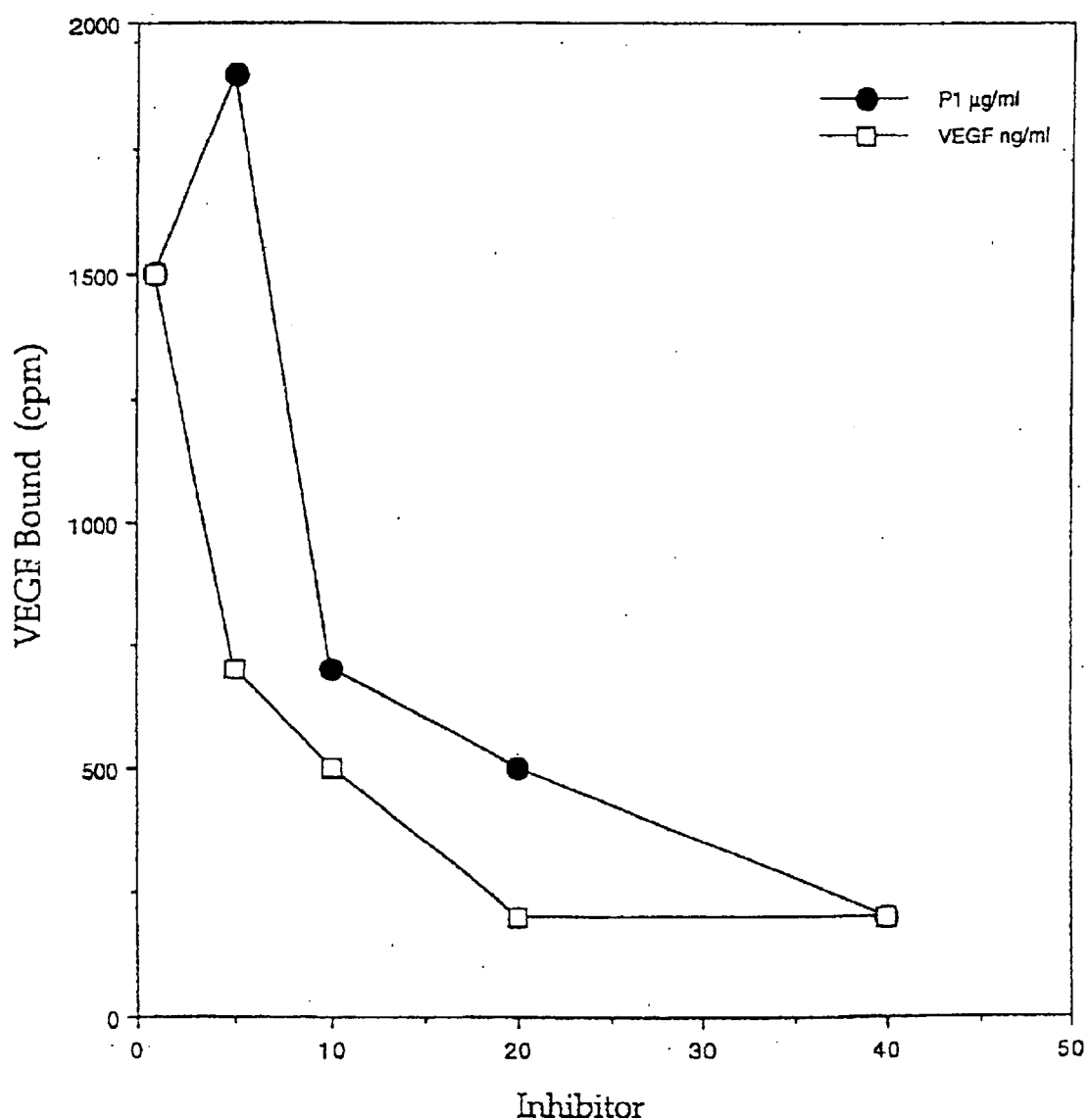
Figure 10B:
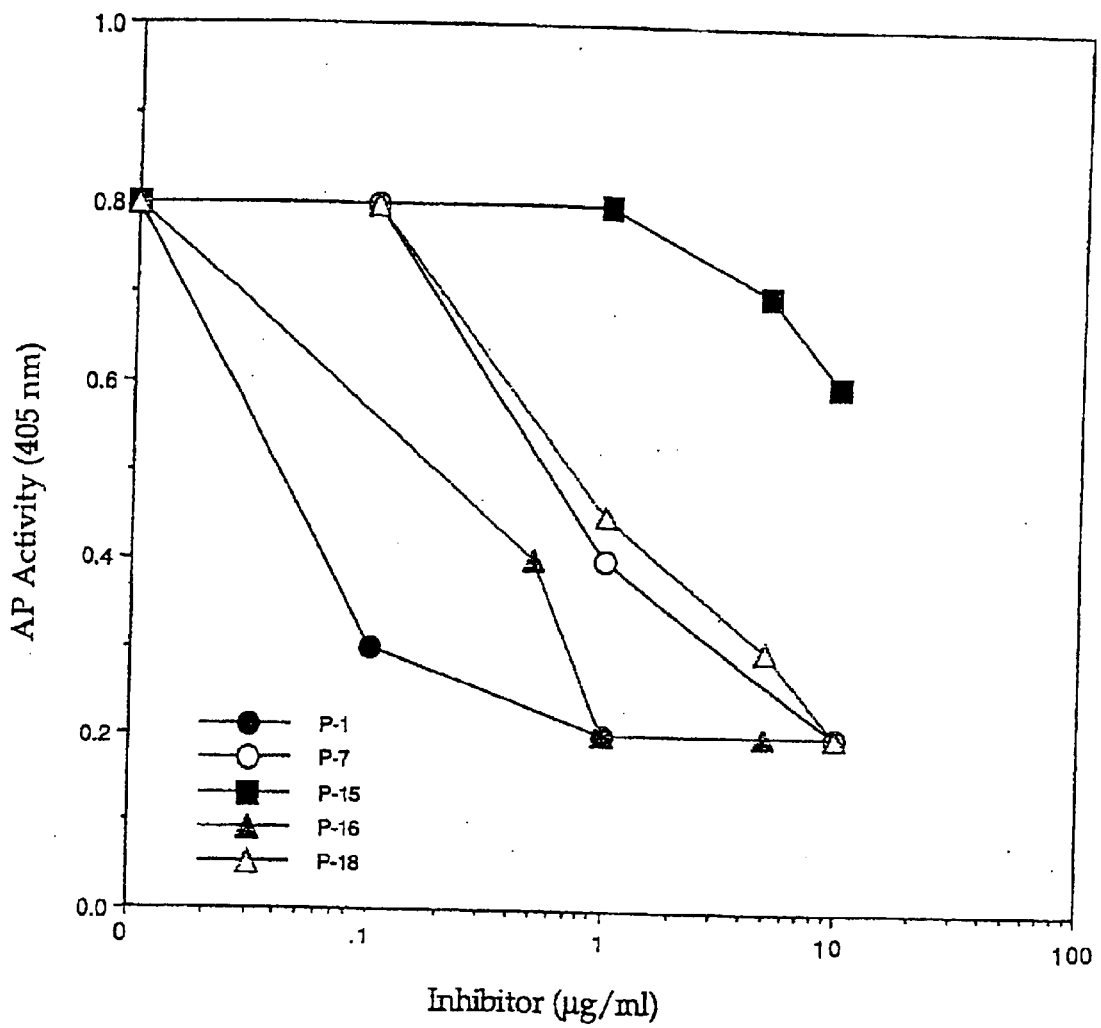

Since both FGF and VEGF share several similar characteristics, such as the requirement of heparin for binding to the receptor (Gitay-Goren et al, 1993) and they may play a synergistic role in tumor angiogenesis, the capacity of P1, P7, P15, P16, P18 to inhibit VEGF binding to its receptors was evaluated. FIG. 10A shows that P1 efficiently inhibits $^{125}$I-VEGF binding to cells highly expressing the KDR/flk-1 VEGF receptor with high potency and has an inhibitory effect similar to that caused by unlabeled VEGF. P1 inhibits VEGF binding to bovine endothelial cells expressing VEGF receptors in a manner similar to the KDR/flk-1-transfected cells (Methods, section x). As can be seen in FIG. 10B, while P1 demonstrated an IC$_{50}$ around 0.04 μM, compounds P15 to P18 were less potent with IC$_{50}$ around 1 μM, when tested in vitro for inhibition of the VEGF receptor flt-1-AP binding to immobilized VEGF, as described in Methods, section (ix).

[II] Example 10

Porphyrin P16 Inhibits the Binding of FGF-9 to FGFR-3

To test the porphyrins for their potential ability to be used for the treatment of FGF receptor-related growth disorders, their activity in FGFR-3 related systems was tested.

Figure 11:
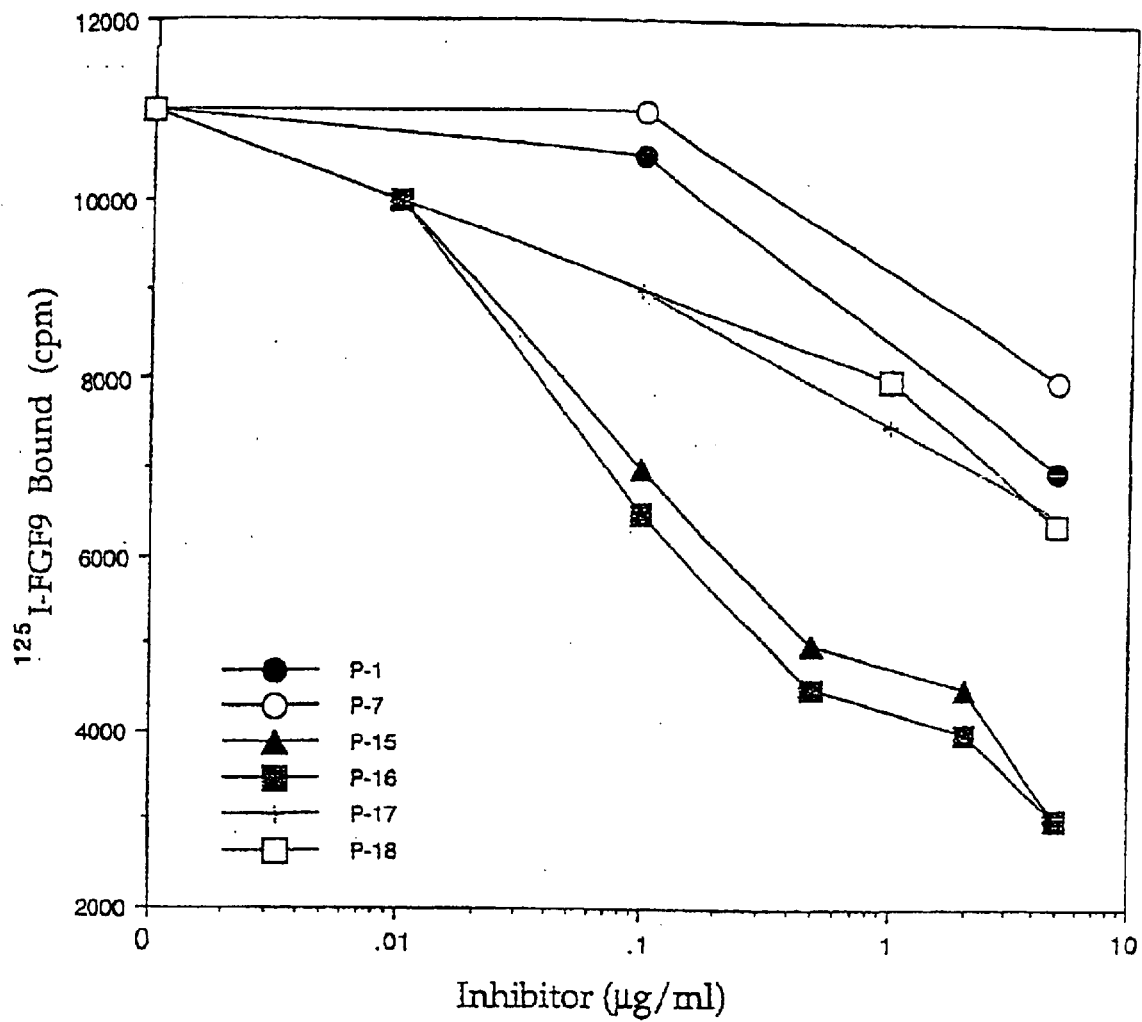
FIG. 11 shows the inhibitory effect of porphyrins on binding of $^{125}$I-FGF9 to immobilized FGFR-3. $^{125}$I-FGF9 (2 ng/ml) was incubated (90 min, 4° C.) with immobilized FGFR-3 as described in Methods, section (iii). Incubations were performed in the presence of 100 ng/ml heparin and increasing concentrations of porphyrins. Non-specific binding was determined in the presence of 100-fold excess of unlabeled bFGF and did not exceed 10% of the total binding. Results represent the mean value in one of at least two independent experiments.

The capacity of the porphyrins P1, P7, P15, P16, P17 and P18 to inhibit FGF-9 induced activity was evaluated by first testing their capability to inhibit FGF-9 binding to FGF receptors in in vitro systems. Thus, the compounds were tested for their capacity to inhibit binding of a soluble FGFR-3 ectodomain alkaline phosphatase fusion protein (FR-3-AP) to FGF-9, utilizing a cell free system, similar to the one described for FGFR-1 in Example 1 above, and measuring the binding of radiolabeled $^{125}$I-FGF-9 to soluble FGFR-3. As shown in FIG. 11, the porphyrins are capable of profoundly inhibiting FGF-9/FGFR-3 binding in the soluble receptor assay in a dose dependent manner with an $IC_{50}$ of 0.1 μg/ml, with P15 and P16 being more potent.

Figure 12:
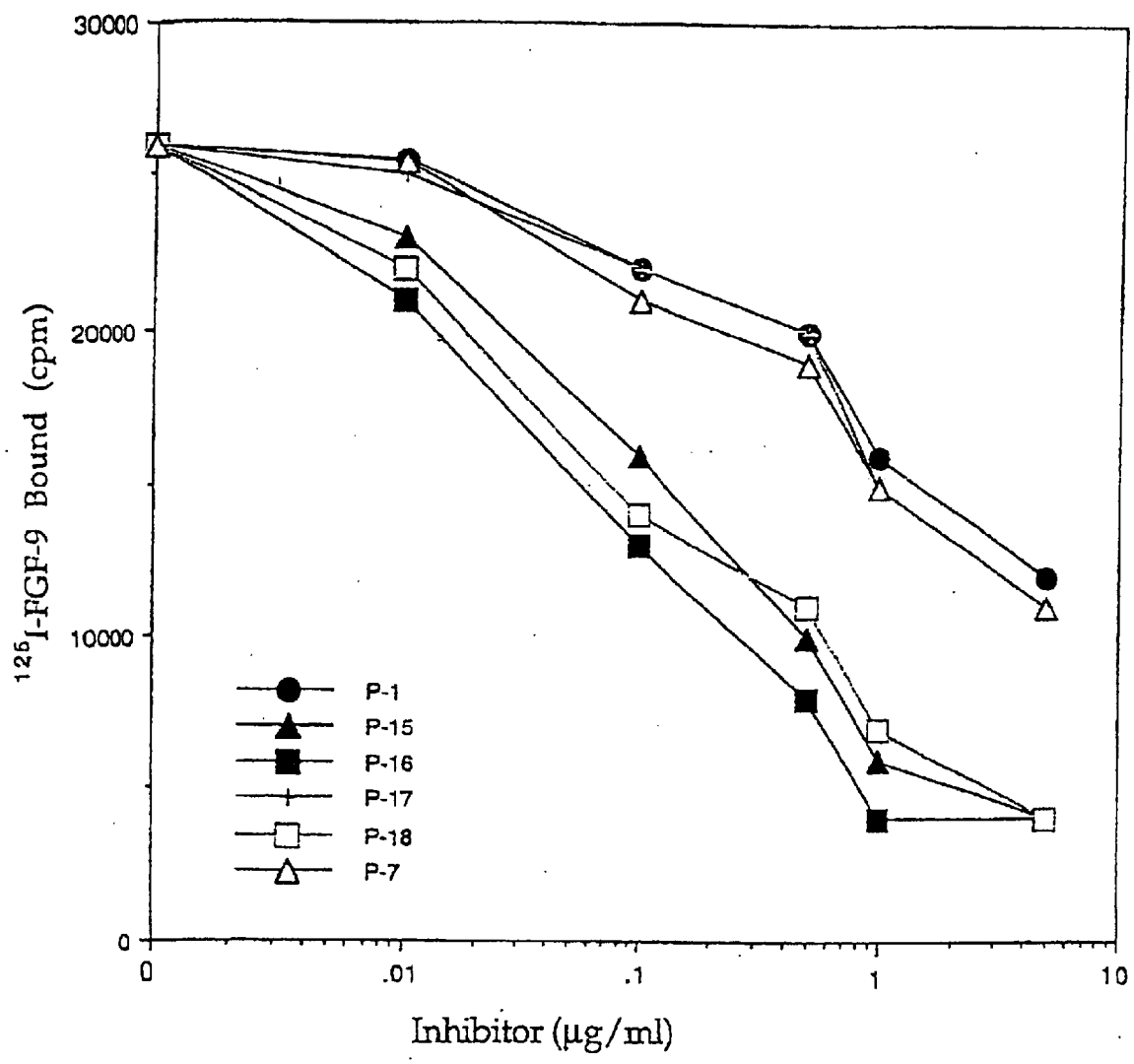
FIG. 12 shows the effect of porphyrins on the binding of $^{125}$I-FGF9 to CHO cells transfected with FGFR-3. CHO mutant cells-745 expressing FGFR-3 were incubated for 90 min at 4° C. in the presence of increasing concentrations of the porphyrins, with 1 μg/ml of heparin and $^{125}$I-FGF9 (2 ng/ml). The binding medium was discarded and the cells were washed with ice cold DMEM/BSA. To determine receptor binding of $^{125}$I-FGF9, the cells were incubated in cold PBS (pH 4) containing 1.6M NaCl and 25 mM HEPES, and the cell extract was counted in a γ-counter. Non-specific binding was determined in the presence of 100-fold excess of unlabeled ligand, and did not exceed 20% of the total bound ligand.

As a second experimental model, CHO cells genetically engineered to express FGFR-3 were used (Hecht et al, 1995), As shown in FIG. 12, also in the cellular receptor system, P16 was more potent, being capable of inhibiting FGF-9 binding with an $IC_{50}$ of 0.1 μg/ml.

[II] Example 11

Porphyrins P1 and P16 Inhibit Mitogenic Activity of FGFR-3 Expressing Cells Induced by FGF-9

Figure 13:
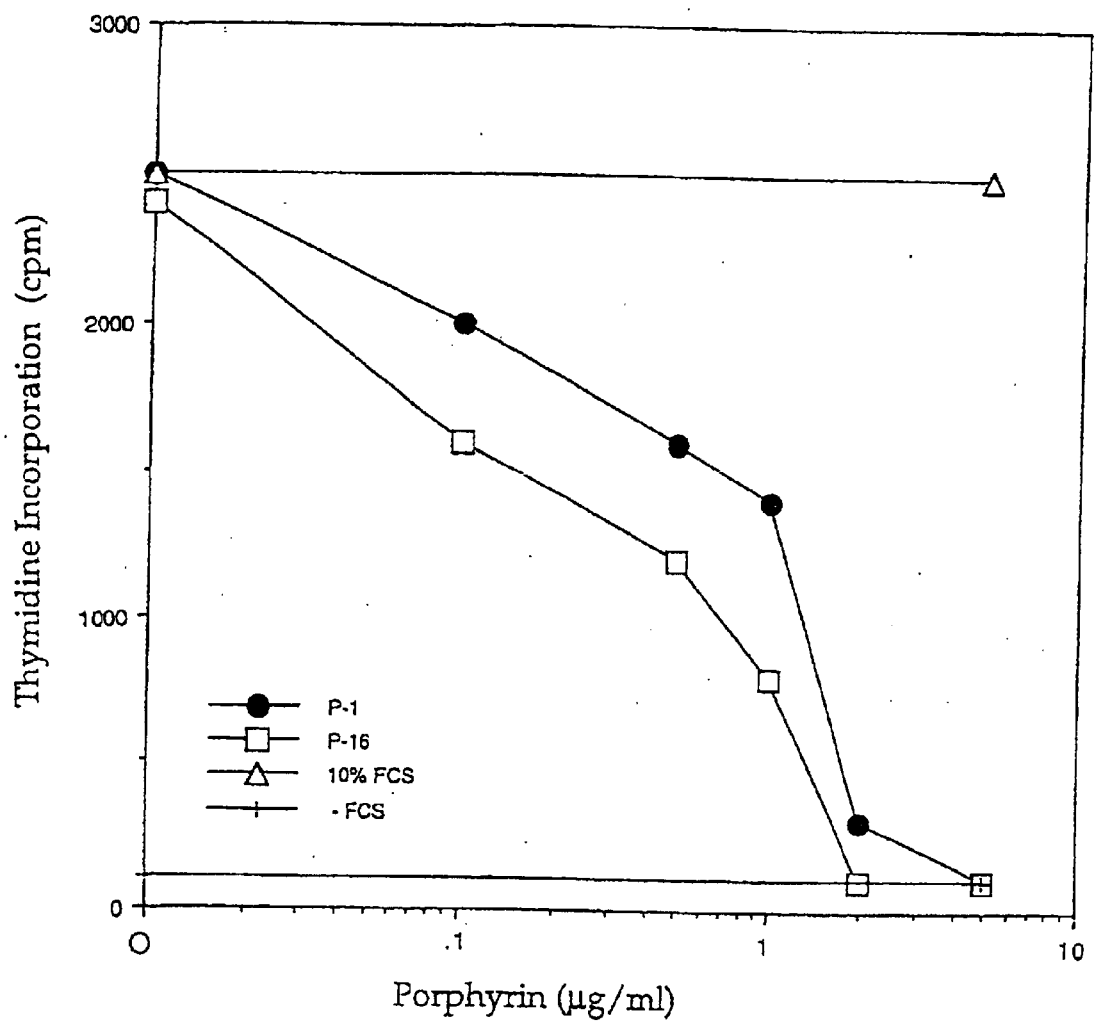
FIG. 13 shows the effect of porphyrins P1 and P16 on FGF-9 induced mitogenic activity of FGFR-3 expressing cells. CHO cells genetically engineered to express FGFR-3 were grown in the presence of increasing concentrations of porphyrins P1 and P16 in order to determine the ability of the porphyrins to inhibit FGF-9 induced DNA synthesis.

CHO cells genetically engineered to express FGFR-3 were used in order to determine the ability of the porphyrins P1 and P16 to inhibit biological activity of FGFR3 as measured by the level of DNA synthesis induced by FGF-9. As can be seen in FIG. 13, both P1 and P16 had a strong inhibitory effect on the cell proliferation induced by FGF-9, indicating that both porphyrins, mote particularly P16, may serve as inhibitors of FGFR-3 unregulated activity.

[II] Example 12

Porphyrin P16 Inhibits FGFR-3 Tyrosine Phosphorylation in Cells Induced by FGF-9

FGFR-3 tyrosine phosphorylation is a distinct parameter of biochemical activation of the receptor leading to signal transduction in the cell nucleus and resulting in biological activity. Measuring the phosphorylation level allows a direct Judgment as to the ability of an inhibitor to effect receptor activation.

Figure 14:
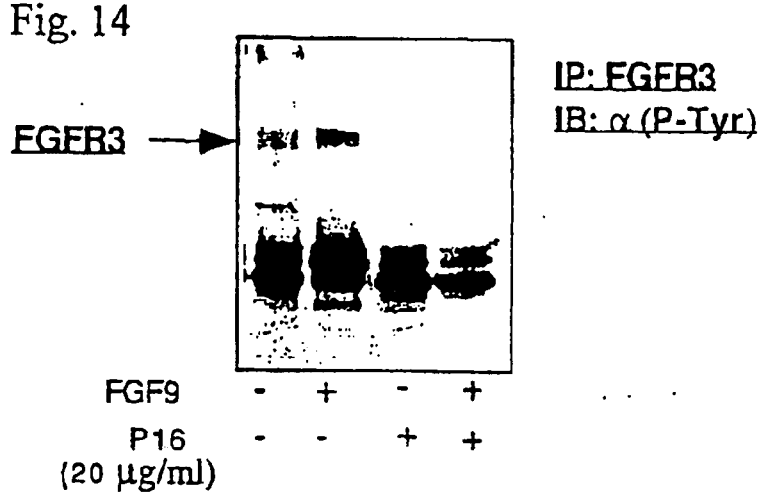
FIG. 14 is an immunoblot showing total FGFR-3 tyrosine phosphorylation induced by FGF-9. Phosphorylation level of FGFR-3 tyrosine kinase in the presence of P16 was demonstrated by immunoprecipitation of FGFR-3 with anti-FGFR-3 antibodies and immunoblotting with anti-phosphotyrosine antibodies.

In order to measure the ability of the porphyrins to inhibit the receptor activation on an enzymatic level as well, FGFR-3 tyrosine phosphorylation was measured in the presence of P16, as described in Methods, section (viii). Immunoprecipitation of FGFR-3 with the anti-FGFR-3 antibodies and immunoblotting with anti-phosphotyrosine antibodies demonstrated that P16 reduced both the basal and, to a much greater extent, the FGF-9 induced phosphorylation of FGFR-3 (FIG. 14), indicating that P16 has a significant, direct and highly specific effect on FGFR-3 activity.

II Example 13

Porphyrin P16 Inhibits PLC-γ and ERK Phosphorylation in FGFR-3 Expressing Cells Induced by FGF-9

Stimulation of FGFR-3 results in a variety of human skeletal genetic defects. The phosphorylated FGFR-3 transduces its signal down stream by transphosphorylation of adaptor proteins which are part of its signaling cascade (Kanai et al, 1997). At least three different FGFR-3 signaling pathways have been identified: 1) the ERK/MAP kinase mediated pathway; 2) the STAT kinase mediated pathway; and 3) the phospholipase C-gamma (PLC-γ) mediated pathway. Examining the level of phosphorylation of these signaling proteins allows one to establish the potency of an inhibitor capable of down regulating FGFR-3 dependent signaling.

Figure 15A:
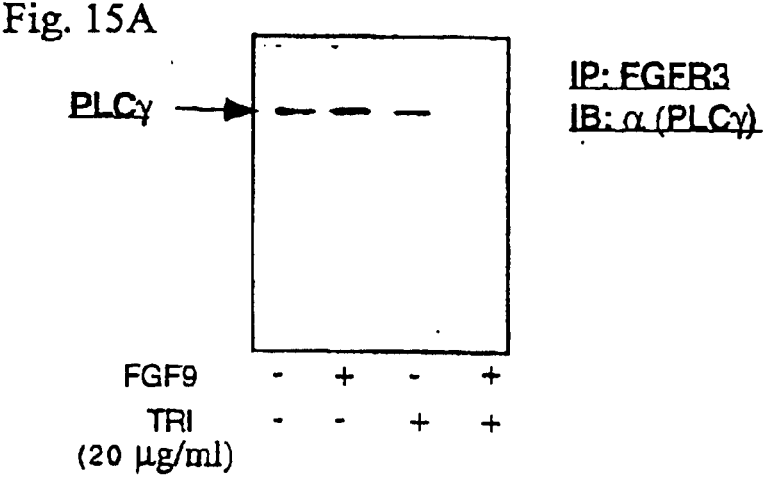
FIGS. 15A–15B show PLC-γ and ERK phosphorylation of FGFR-3 expressing cells induced by FGF-9. Phosphorylation level of PLC-γ (FIG. 15A) and ERK (FIG. 15B) in the presence of FGF9 and P16 was examined by immunoblotting with anti-PLC-γ or activated ERK antibodies.
Figure 15B:
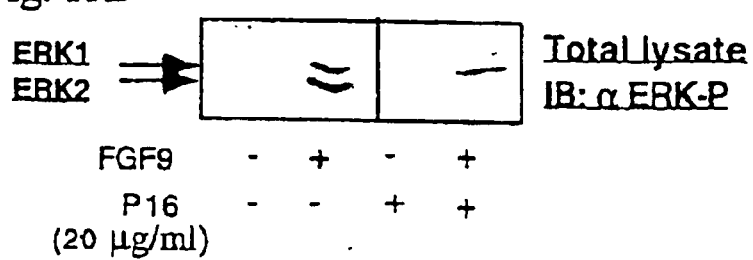

In order to demonstrate the effect of P16 on the Enzymatic signal transduction pathway induced by FGFR-3, phosphorylation of PLC-γ and ERK, two well established players in FGF signaling, was examined in cells expressing FGFR-3. Immunoblotting with anti-PLC-γ antibodies (FIG. 15A) or anti-activated ERK/MAP kinase antibodies (FIG. 15B), respectively, demonstrated clear reduction in the activation of both signal-mediating proteins by P16. These findings support the notion that the porphyrins can serve for treating FGFR-3 related growth disorders. ERK1 and ERK2 are two isoforms of ERK.

II Example 14

P1 Inhibits Smooth Muscle Cells Proliferation Induced by bFGF

Figure 16:
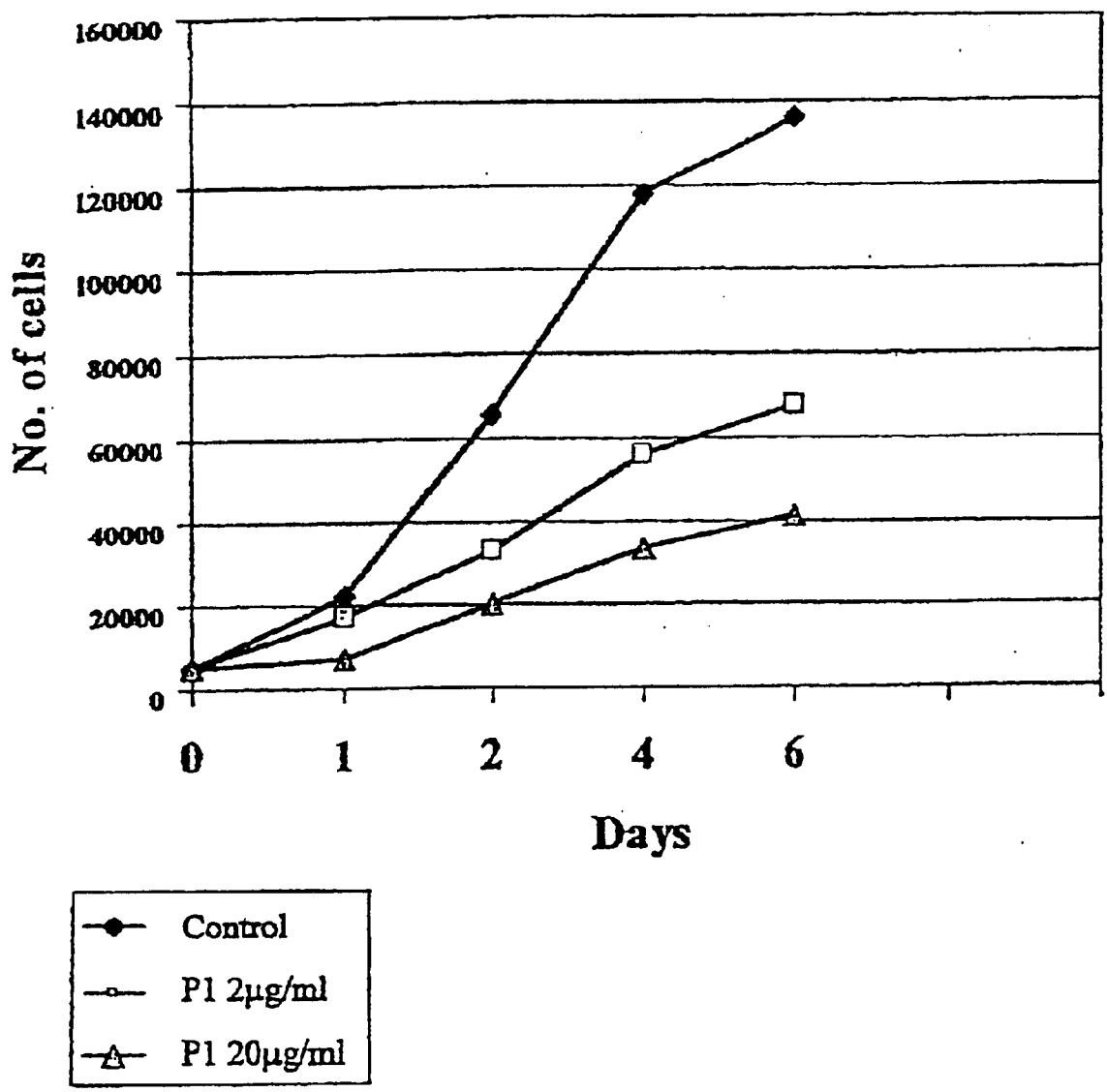
FIG. 16 shows the inhibitory effect of P1 on bFGF-induced mitogenic activity of smooth muscle cells.

In order to determine the ability of P1 to inhibit the biological activity of bFGF on cell proliferation, smooth muscle cells were grown in 24-well plates in the presence of bFGF (10 ng/ml) and in the presence of 2 μg/ml or 20 μg/ml of P1. Cell number was determined daily by counting cell samples under a microscope. As can be seen in FIG. 16, P1 had a strong inhibitory effect on smooth muscle cell proliferation induced by bFGF. These results suggest that P1 may serve as an inhibitor of smooth muscle cells causing restenosis.

TABLE 1

Inhibitory activity in vitro (IC50 in μM) of compounds P1–P21 on binding of FGF to FGFR

| Compound | Cellular receptor binding[1] | Soluble receptor binding[2] | Screen AP assay[3] |
|---|---|---|---|
| P1 | 1.5 | 0.75 | 0.075 |
| P2 | ND | ND | NA |
| P3 | ND | ND | NA |
| P4 | ND | ND | NA |
| P5 | 1.8 | 0.9 | 0.1 |
| P6 | 1,8 | 0.7 | 0.09 |
| P7 | 2 | 0.8 | 0.07 |
| P8 | 1.3 | 0.95 | 0.095 |
| P9 | 5.5 | 3 | NA |
| P10 | 1.9 | 0.85 | 0.08 |
| P11 | NA | ND | 0.5 |
| P12 | NA | 10 | ND |
| P13 | NA | NA | ND |
| P14 | 3 | 0.85 | ND |
| P15 | 0.12 | 0.08 | ND |
| P16 | 0.02 | 0.01 | ND |
| P17 | 0.03 | 0.02 | ND |
| P18 | 0.1 | 0.075 | ND |
| P19 | 2 | ND | 0.1 |
| P20 | 0.2 | ND | 0.03 |
| P21 | 1 | ND | ND |

[1]Assay according to Methods, section (iv)
[2]Assay according to Methods, section (iii)
[3]Assay according to Methods, section (ii)
ND - not determined; NA - not active at 10 μM

TABLE 2

Inhibitory Activity in vivo of Compounds P1–P21 in the LLC murine tumor model. (as % of total Inhibition at 25 μg/gram)

| Number | LLC tumor model |
|---|---|
| P1 | 100 |
| P2 | ND |
| P3 | ND |
| P4 | ND |

TABLE 2-continued
Inhibitory Activity in vivo of Compounds P1–P21 in the LLC murine tumor model. (as % of total Inhibition at 25 μg/gram)
| Number | LLC tumor model |
|---|---|
| P5 | 75 |
| P6 | ND |
| P7 | 90 |
| P8 | 90 |
| P9 | ND |
| P10 | ND |
| P11 | ND |
| P12 | 0 |
| P13 | ND |
| P14 | 90 |
| P15 | ND |
| P16 | 60 |
| P17 | 40 |
| P18 | 50 |
| P19 | ND |
| P20 | 150 |
| P21 | 200 |
ND — not determined
APPENDIX A
Structures of Compounds P-1-P-21
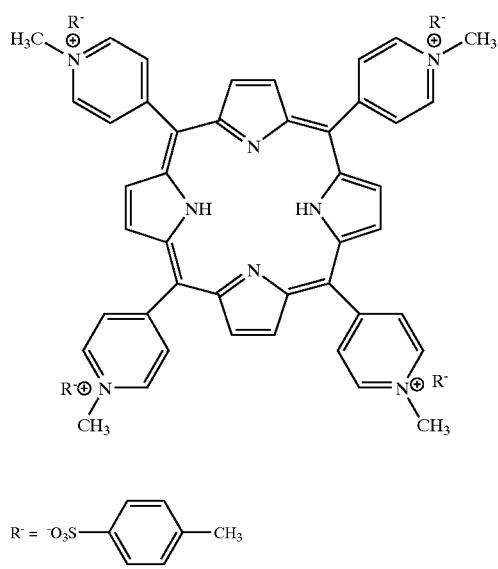
P-1
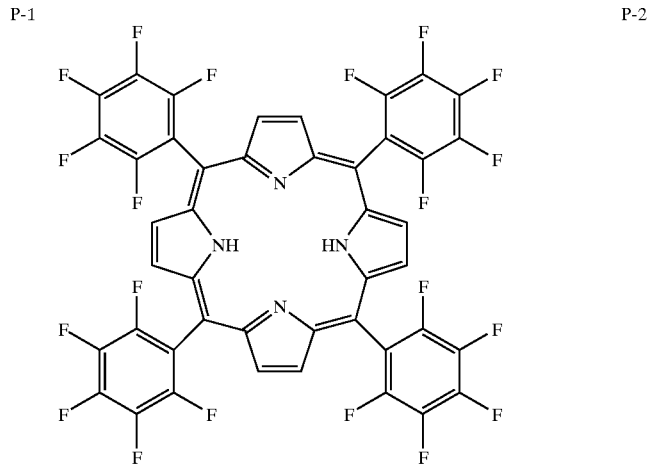
P-2
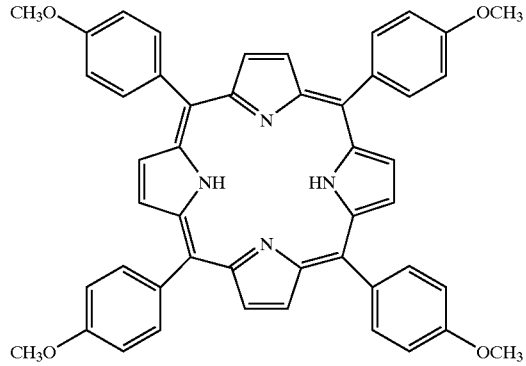
P-3

-continued
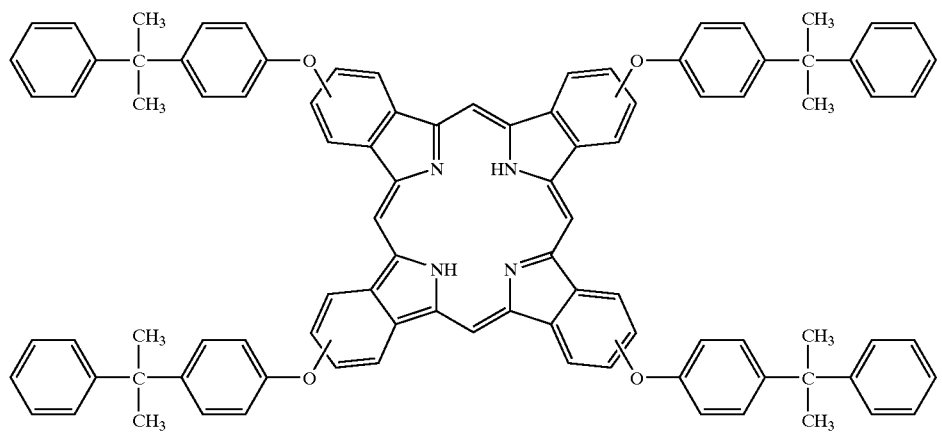
P-4
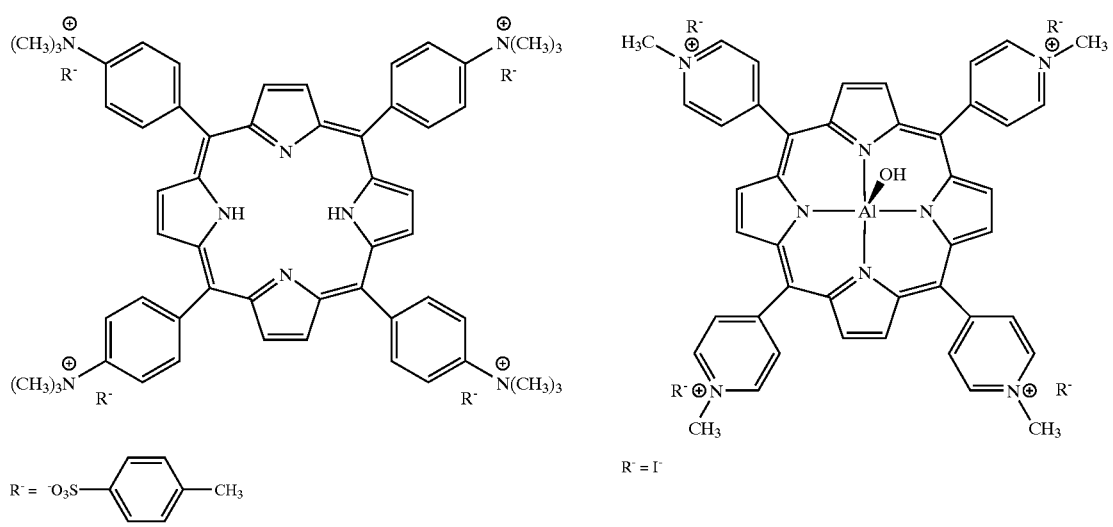
P-5    P-6
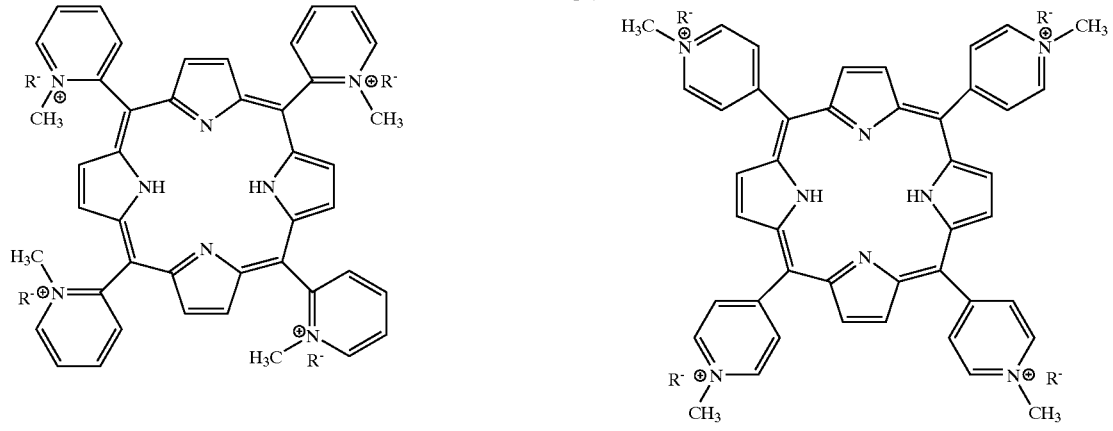
P-7    P-8

-continued
P-9
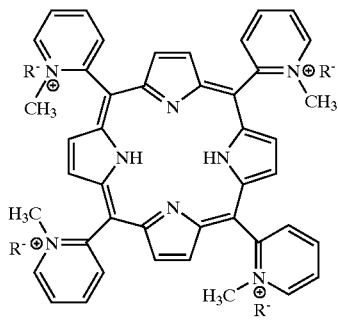
R⁻ = ⁻O₃S—⟨ ⟩—CH₃
P-10
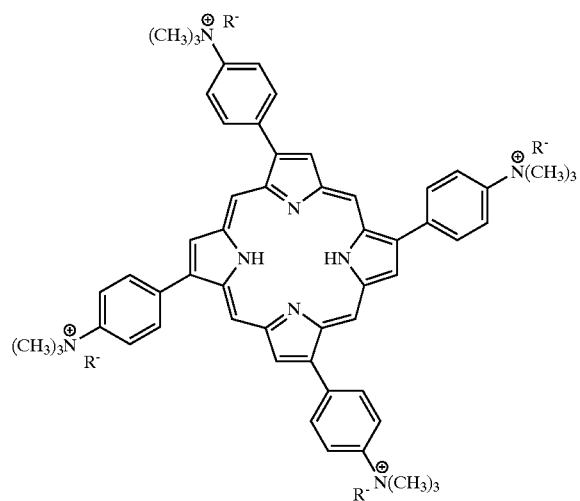
P-11
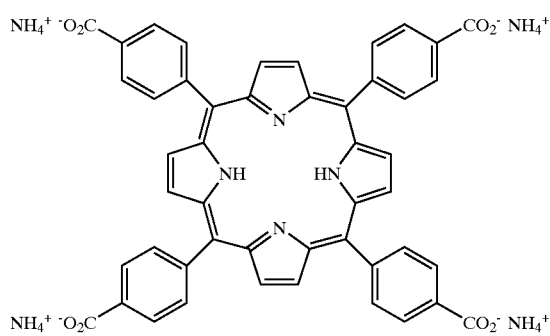
P-12
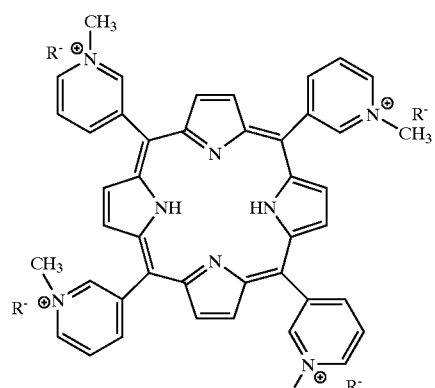
R⁻ = ⁻O₃S—⟨ ⟩—CH₃
P-13
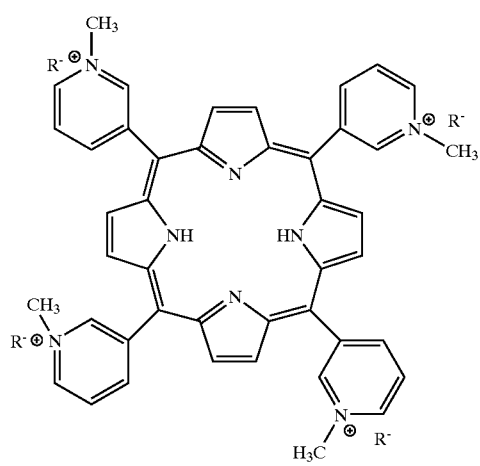
R⁻ = I⁻
P-15
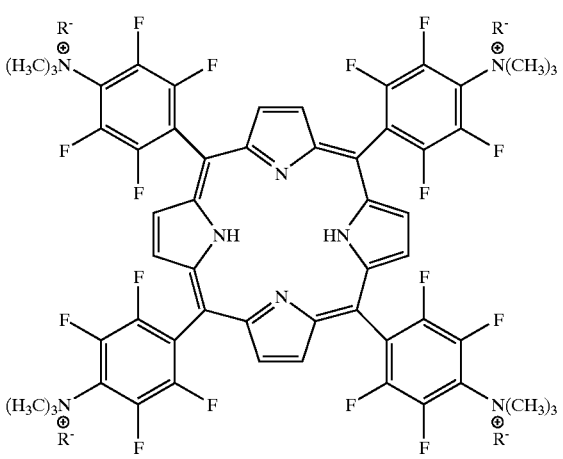
R⁻ = CF₃SO₃

-continued

P-16
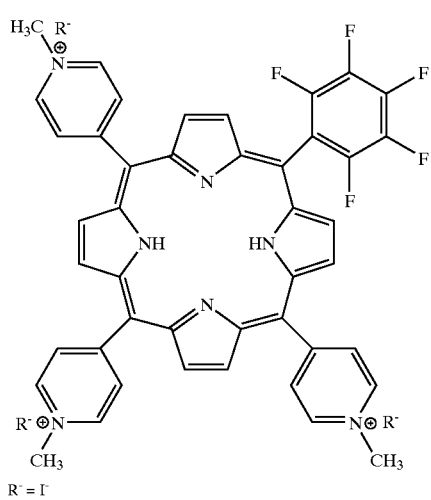

P-17
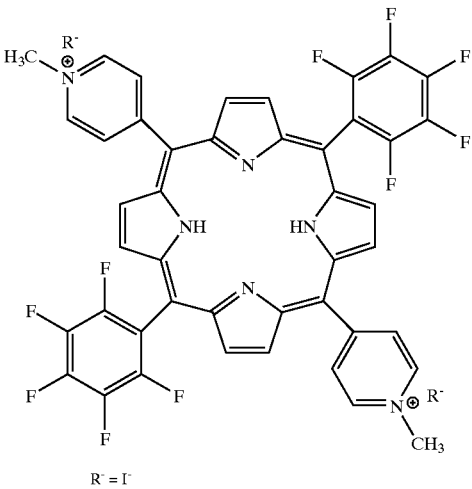

P-18
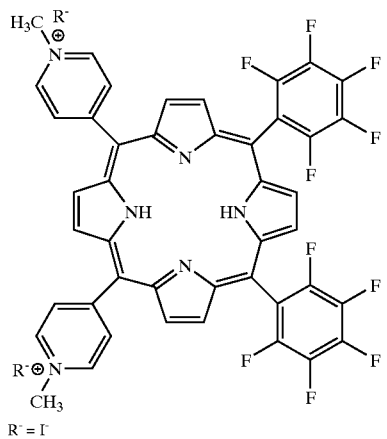

P-19
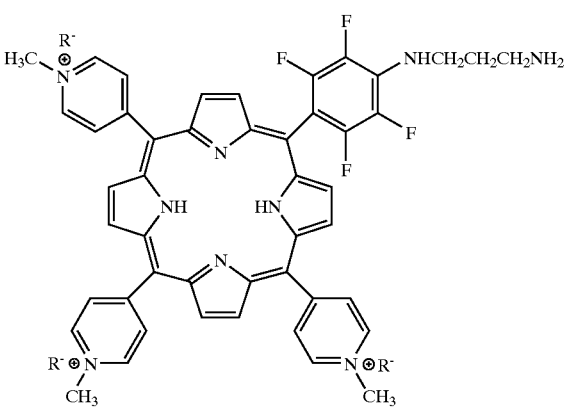

P-20
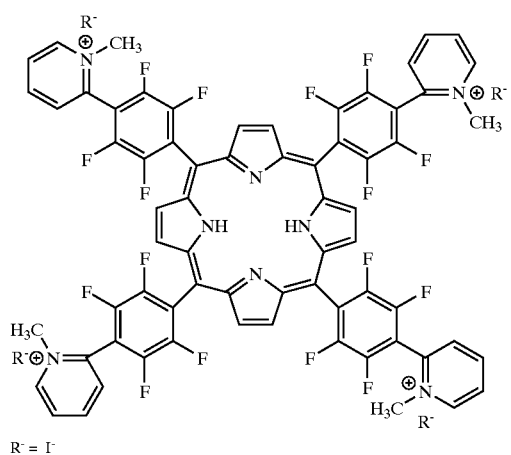

P-21
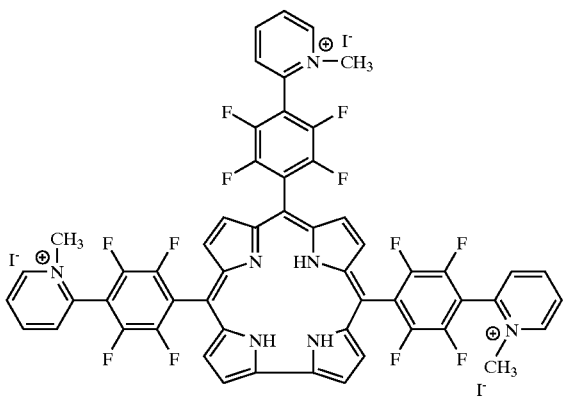

References

1. Aloe L, Bracci-Laudiero L, Bonini S, Manni L (1997) The expanding role of nerve growth factor: from neurotrophic activity to immunologic diseases. Allergy 52(9):883–94.

2. Aviezer, D., Levy, E., Safran, M., Svahn, C., Buddecke, E., Schmidt, A., David, G., Vlodavsky, I. and Yayon, A. (1994a). Differential spectral requirements of heparin and heparan sulfate proteoglycans that promote binding of basic fibroblast growth factor to its receptor. J Biol Chem, 269, (1) 114–21.

3. Aviezer, D., Hecht, D., Safan, M., Eisinger, M., David, G. and Yayon, A. (1994b). Perlecan, basal lamina proteoglycan, promotes bFGF-receptor binding, mitogenesis and angiogenesis. Cell, 79, 1005–1013.
4. Aviezer, D. and Yayon, A. (1994). Hepain-dependent binding and autophosphorylation of epidermal growth factor (EGF) receptor by heparin-binding EGF-like growth factor but not by EGF. Proc Natl Acad Sci USA, 91, (25) 12173–7.
5. Connor B, Dragunow M (1998) The role of neuronal growth factors in neurodegenerative disorders of the human brain. Brain Res Brain Res Rev; 27(1):1–39.
6. Deng, C., Wynshaw, B.A., Zhou, F., Kuo, A. and Leder, P. (1996). Fibroblast growth factor receptor 3 is a negative regulator of bone growth. Cell, 84, (6) 911–21.
7. Dougherty T J, Gomer C J, Henderson B W, Jori G, Kessel D, Korbelik M, Moan J, Peng Q (1998) Photodynamic Therapy J Natl Cancer Inst; 90(12):889–905.
8. Folkman, J. (1989) Successful treatment of an angiogenic disease. N Engl J Med; 320(18): 1211–2.
9. Fong T A, Shawver L K, Sun L, Tang C, App H, Powell T J, Kim Y H, Schreck R, Wang X, Risau W. Ulrich A, Hirth K P, McMahon G. SU5416 is a potent and selective inhibitor of the vascular endothelial growth factor receptor (Flk-1/KDR) that inhibits tyrosine kinase catalysis, tumor vascularization, and growth of multiple tumor types. Cancer Res. 59: 99–106, 1999.
10. Frade J M, Barde Y A (1998) Nerve growth factor: two receptors, multiple functions. Bioessays 20(2):137–45.
11. GitayGoren, I, Soker, S., Vlodavsky, I. and Neufeld, G. (1992). The binding of vascular endothelial growth factor to its receptors is dependent on cell surface-associated heparin-like molecules. J. Biol. Chem., 267, (9) 6093–6098.
12. Gross Z., Galili N. and Saltsman I. The First Direct Synthesis of Corroles from Pyrrole. Angew. Chem. Int Ed. Eng., 38, 1427–9, 1999.
13. Guimond, S., Maccaran M., Olwin, B. B., Lindahl, U. and Rapraeger, A. C. (1993). Activating and inhibitory heparin sequences for FGF-2 (basic FGF). Distinct requirements for FGF-1, FGF-2 and FGF4. J Biol Chem, 268 (32): 23906–14.
14. Hecht, D., Zimmerman, N., Bedford, M., Avivi, A. and Yayon, A (1995). Identification of fibroblast growth factor 9 (FGF9) as a high affinity, heparin dependent ligand for FGF receptors 3 and 2 but not for FGF receptors 1 and 4. Growth Factors, 12, (3) 223–33.
15. Jori G, Reddi E (1993) The role of lipoproteins in the delivery of tumour-targeting photosensitizers. Int J Biochem 10 1369–1375.
16. Jori G, Reddi E, Cozzani I, Tomio L (1986) Controlled targeting of different subcellular sites by porphyrins in tumour-bearing mice. Br J Cancer 53(5):615–621.
17. Kanai, M., Goke M., Tsunekawa S., Podolsky D. K. (1997). Signal transduction pathway of human fibroblast growth factor receptor 3. Identification of a novel 66-kDa phosphoprotein. J. Biol. Chem, 272(10): 6621–8.
18. Klagsbrun, M. (1989). The fibroblast growth factor family: structural and biological properties. Progress in Growth Factor Research, 1, 207–235.
19. La, T., Miskelly, G., Bau, R. (1997) Inorg. Chem. 36, 5321.
20. Margaron P, Madanas P, Quellet R, Van Lier J E Biological activities of phthalocyanines. XVII histopathologic evidence for different mechanisms of EMT-6 tumor necrosis induced by photodynamic therapy with disulfonated aluminum phthalocyanine or photofrin. Anticancer Res., 16:613–20, 1996.
21. Miao H Q, Ornitz D M, Aingorn E, Ben-Sasson S A, Vlodavsky I, Modulation of fibroblast growth factor-2 receptor binding, dimerization, signaling and angiogenic activity by a synthetic heparin-mimicking polyanionic compound. J Clin Invest, 99:1565–75, 1997.
22. Mohammadi M, McMahon G. Sun L, Tang C, Hith P, Yeh B K, Hubbard S R, Schlessinger J Structures of the tyrosine kinase domain of fibroblast growth factor receptor in complex with inhibitors. Science; 276, :955–60, 1997.
23. Naski, M. C., Wang, Q., Xu, J. and Ornitz, D. M. (1996). Graded activation of fibroblast growth factor receptor 3 by mutations causing achondroplsia and thanatophoric displasia Nature Genetics, 13, 233–237.
24. Nicosia R F, Ottinetti A, (1990) Growth of microvessels in serum-free matrix culture of rat aorta. A quantitative assay of angiogenesis in vitro. Lab Invest 63(1):115–122.
25. O'Reilly, M. S., Holmgren, L., Shing, Y., Chen, C., Rosenthal, R. A., Moses, M., Lane, W. S., Cao, Y., Sage, E. H., Folkman, J. (1994) Angiostatin: a novel angiogenesis inhibitor that mediates the suppression of metastases by a Lewis lung carcinoma. Cell 79(2): 315–28.
26. Ornitz, D. M., Yayon, A., Flangan, J. G., Svahn, C. M., Levi, E. and Leder, P. (1992). Heparin is required for cell-free binding of basic fibroblast growth factor to a soluble receptor and for mitogenesis in whole cells. Mol. Cell. Biol., 12, 240–247.
27. Ornitz, D. M., Herr, A. B., Nilsson, M., Westman, J., Svahn, C. M. and Waksman, G. FGF binding and FGF receptor activation by synthetic heparan-derived di- and trisaccharides. Science. 268, 432–6, 1995.
28. Patt, S., Danner, S., Theallier-Janko, A., Breier, G., Hottenrott, G., Plate, K. H., Cervos-Navarro, J. (1998) Upregulation of vascular endothelial growth factor in severe chronic brain hypoxia of the rat Neurosci Lett 252(3): 199–202.
29. Rapraeger, A. C., Krufka, A. and Olwin, B. B. (1991). Requirement of heparan sulfate for bFGF-mediated fibroblast growth and myoblast differentiation. Science, 252, 1705–17.
30. Reardon, W., Winter, R. M., Rutland, P., Puileyn, L. J., Jones, B. M. and Malcolm, S. (1994). Mutations in the fibroblast growth factor receptor 2 gene cause Crouzon syndrome. Nature Genetic, 3, 98–103.
31. Roeckl, W., Hecht, D., Sztajer, H., Waltenberger, J., Yayon, A., Weich, H. A. (1998) Differential binding characteristics and cellular inhibition by soluble VEGF receptors 1 and2. Exp Cell Res, 241(1): 161–70.
32. Rousseau, F., Bonaventure, J., Legeal-Mallet, L., Pelet, A., Rozet, J.-M., Maroteaux, P., Le-Merrer, M. and Munnich, A. (1994). Mutations in the gene encoding fibroblast growth factor receptor-3 in achondroplasia Nature, 371, 252–254.
33. Schlessinger, J., Lax, I. and Lemmon, M. Regulation of growth factor activation by proteoglycans: what is the role of the low affinity receptors? Cell, 83, 357–60, 1995.
34. Shiang, R, Thompson, L. M., zhu, Y.-Z., Church, D. M., Winokur, S. T. and Wasmuth, J. J. (1994). Mutations in transmembrane domain of FGFR3 cause the most common genetic form of dwarfism, Achondroplasia Cell, 78, 335–342.
35. Ulhrich, A. and Schlessinger, J. (1990). Signal transduction by receptors with tyrosine kinase activity. Cell, 61, 203–212.
36. Van de Woude G F, Jeffers M, Cortner J, Alvord.G, Tsarfaty I, Resau J (1997) Met-HGF/SF: tumorigenesis, invasion and metastasis. Ciba Found Symp; 212:119–130.

37. Yanagawa K, Yamashita T, Yada K, Ohira M, Ishikawa T, Yano Y, Otani S, Sowa M (1998) The antiproliferative effect of HGF on hepatoma cells involves induction of apoptosis with increase in intracellular polyamine concentration levels. Oncol Rep 5(1):185–190.
38. Yayon, A. and Klagsbrun, M. (1990). Autocrine transformation by chimeric signal peptide-basic fibroblast growth factor: Reversal by suramin. Proc. Natl. Acad. Sci. USA, 87, 5346–5350.
39. Yayon, A., Klagsbrun, M., Esko, J. D., Leder, P. and Omitz, D. M. (1991). Cell surface, heparin-like molecules are required for binding of basic fibroblast growth factor to its high affinity receptor. Cell, 64, 841–848.

What is claimed is:

1. A pharmaceutical composition comprising a pharmaceutically acceptable carrier and a 5,10,15-triaryl-corrole of the formula:

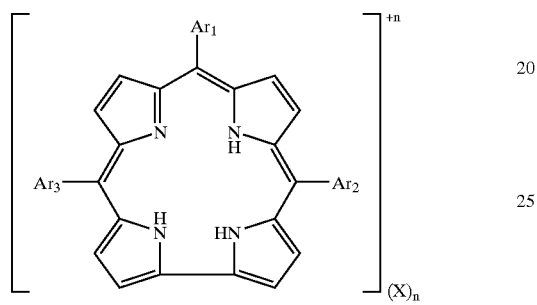

wherein $Ar_1$, $Ar_2$, and $Ar_3$, the same or different, are each an aryl radical selected from the group consisting of a carboaryl, a heteroaryl and a mixed carboaryl-heteroaryl radical, wherein said carboaryl radical by itself or as part of a mixed carboaryl-heteroaryl radical is selected from the group consisting of phenyl, biphenyl and naphthyl substituted by one or more halogen atoms, and/or one or more $C_1$–$C_8$ alkyl, $C_1$–$C_8$ alkoxy, $C_1$–$C_8$ alkylamino, amino-($C_1$–$C_8$)alkylamino, and tri-($C_1$–$C_8$) alkylammonium radicals, and said heteroaryl radical by itself or as part of a mixed carboaryl-heteroaryl radical is selected from the group consisting of furyl, thienyl, pyrrolyl, imidazolyl, thiazolyl, pyridyl, pyrimidyl, and triazinyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, and wherein at least two of said aryl radicals are positively charged, n is an integer from 2 to 3 and X is a pharmaceutically acceptable anion.

2. The pharmaceutical composition according to claim 1, wherein said carboaryl radical is phenyl substituted by fluoro and optionally by tri-($C_1$–$C_8$) alkylammonium or amino-($C_1$–$C_8$) alkylamino.

3. The pharmaceutical composition according to claim 2, wherein one or two of said carboaryl radicals is pentafluorophenyl and/or 4-aminopropylamino-2,3,5,6-tetrafluorophenyl.

4. The pharmaceutical composition according to claim 2, wherein one to three of said carboaryl radicals is 4-trimethylammoniophenyl or 4-trimethylammonio-2,3,5,6-tetrafluorophenyl.

5. The pharmaceutical composition according to claim 1, wherein one to three of said heteroaryl radicals is N-($C_1$–$C_8$ alkyl)-pyridylium.

6. The pharmaceutical composition according to claim 5, wherein said radical is selected from the group consisting of 2-, 3- and 4-(N-methyl) pyridylium.

7. The pharmaceutical composition according to claim 1, wherein said mixed carboaryl-heteroaryl radical is 4-(N-methyl-2-pyridylium)-2,3,5,6-tetrafluorophenyl.

8. The pharmaceutical composition according to claim 7, wherein the 5,10,15-triaryl-corrole is the compound 5,10,15-tris[2,3,5,6-tetrafluorophenyl-4-(N-methyl-2-pyridylium)]-21H,23H-corrole triiodide.

9. A method for inhibiting growth factor receptor tyrosine kinase activity in a patient in need thereof, which comprises administering to said patient a tetrapyrrolic macrocycle selected from the group consisting of:

(a) a 5,10,15,20-tetraaryl-porphyrin of the formula:

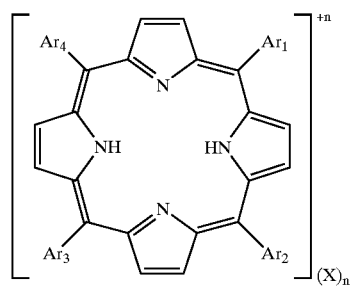

wherein $Ar_1$, $Ar_2$, $Ar_3$, and $Ar_4$, the same or different, are each an aryl radical selected from the group consisting of a carboaryl, a heteroaryl and a mixed carboaryl-heteroaryl radical, wherein said carboaryl radical by itself or as part of a mixed carboaryl-heteroaryl radical is selected from the group consisting of phenyl, biphenyl and naphthyl substituted by one or more halogen atoms, and/or one or more $C_1$–$C_8$ alkyl, $C_1$–$C_8$ alkoxy, $C_1$–$C_8$ alkylamino, amino-($C_1$–$C_8$)alkylamino, and tri-($C_1$–$C_8$) alkylammonium radicals, and said heteroaryl radical by itself or as part of a mixed carboaryl-heteroaryl radical is selected from the group consisting of furyl, thienyl, pyrrolyl, imidazolyl, thiazolyl, pyridyl, pyrimidyl, and triazinyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, wherein at least two of said $Ar_1$, $Ar_2$, $Ar_3$, and $Ar_4$ aryl radicals are positively charged, n is an integer from 2 to 4 and X is a pharmaceutically acceptable anion, provided that at least two of said at least two positively charged $Ar_1$, $Ar_2$, $Ar_3$, and $Ar_4$ aryl radicals are selected from the group consisting of N-($C_1$–$C_8$)alkyl-pyridylium, 4-tri($C_1$–$C_8$) alkylammonium)-2,3,5,6-tetrafluorophenyl and 4-N-($C_1$–$C_8$)alkyl-pyridylium)-2,3,5,6-tetrafluorophenyl and, when at least two of said positively charged $Ar_1$, $Ar_2$, $Ar_3$, and $Ar_4$ radicals are N-($C_1$–$C_8$)alkyl-pyridylium, at least one of the remaining $Ar_1$, $Ar_2$, $Ar_3$, and $Ar_4$ is a non-positively charged aryl radical selected from the group consisting of pentafluorophenyl and 4-amino($C_1$–$C_8$)alkylamino-2,3,5,6-tetrafluorophenyl; and (b) 5,10,15-triaryl-corrole of the formula:

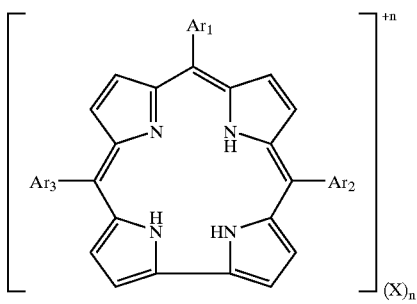

wherein $Ar_1$, $Ar_2$, and $Ar_3$, the same or different, are each an aryl radical selected from the group consisting of a carboaryl, a heteroaryl and a mixed carboaryl-heteroaryl radical, wherein said carboaryl radical by itself or as part of a mixed carboaryl-heteroaryl radical is selected from the group consisting of phenyl, biphenyl and naphthyl substituted by one or more halogen atoms, and/or one or more $C_1$–$C_8$ alkyl, $C_1$–$C_8$ alkoxy, $C_1$–$C_8$ alkylamino, amino-($C_1$–$C_8$)alkylamino, and tri-($C_1$–$C_8$) alkylammonium radicals, and said heteroaryl radical by itself or as part of a mixed carboaryl-heteroaryl radical is selected from the group consisting of furyl, thienyl, pyrrolyl, imidazolyl, thiazolyl, pyridyl, pyrimidyl, and triazinyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, and wherein at least two of said aryl radicals are positively charged, n is an integer from 2 to 3 and X is a pharmaceutically acceptable anion;

in an amount sufficient to inhibit growth factor receptor tyrosine kinase activity.

10. A method according to claim 9 which comprises administration of a 5,10,15,20-tetraaryl-porphyrin of the formula:

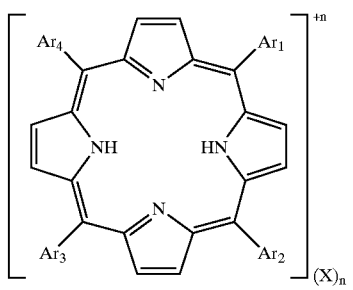

wherein $Ar_1$, $Ar_2$, $Ar_3$, and $Ar_4$, the same or different, are each an aryl radical selected from the group consisting of a carboaryl, a heteroaryl and a mixed carboaryl-heteroaryl radical, wherein said carboaryl radical by itself or as part of a mixed carboaryl-heteroaryl radical is selected from the group consisting of phenyl, biphenyl and naphthyl substituted by one or more halogen atoms, and/or one or more $C_1$–$C_8$ alkyl, $C_1$–$C_8$ alkoxy, $C_1$–$C_8$ alkylamino, amino-($C_1$–$C_8$)alkylamino, and tri-($C_1$–$C_8$) alkylammonium radicals, and said heteroaryl radical by itself or as part of a mixed carboaryl-heteroaryl radical is selected from the group consisting of furyl, thienyl, pyrrolyl, imidazolyl, thiazolyl, pyridyl, pyrimidyl, and triazinyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, wherein at least two of said $Ar_1$, $Ar_2$, $Ar_3$, and $Ar_4$ aryl radicals are positively charged, n is an integer from 2 to 4 and X is a pharmaceutically acceptable anion, provided that at least two of said at least two positively charged $Ar_1$, $Ar_2$, $Ar_3$, and $Ar_4$ aryl radicals are selected from the group consisting of N-($C_1$–$C_8$)alkyl-pyridylium, 4-tri($C_1$–$C_8$)alkylammonium)-2,3,5,6-tetrafluorophenyl and 4-N-($C_1$–$C_8$)alkyl-pyridylium)-2,3,5,6-tetrafluorophenyl and, when at least two of said positively charged $Ar_1$, $Ar_2$, $Ar_3$, and $Ar_4$ radicals are N-($C_1$–$C_8$)alkyl-pyridylium, at least one of the remaining $Ar_1$, $Ar_2$, $Ar_3$, and $Ar_4$ is a non-positively charged aryl radical selected from the group consisting of pentafluorophenyl and 4-amino($C_1$–$C_8$)alkylamino-2,3,5,6-tetrafluorophenyl, in an amount sufficient to inhibit said growth factor receptor tyrosine kinase activity.

11. The method according to claim 10, wherein one or two of said carboaryl radicals is pentafluorophenyl and/or 4-aminopropylamino-2,3,5,6-tetrafluorophenyl.

12. The method according to claim 10, wherein said carboaryl radical is phenyl substituted by fluoro and optionally by tri-($C_1$–$C_8$) alkylammonium.

13. The method according to claim 11, wherein one to two of said carboaryl radicals is 4-trimethylammonio-2,3,5,6-tetrafluorophenyl.

14. The method according to claim 10, wherein said mixed carboaryl-heteroaryl radical is 4-(N-methyl-2-pyridylium)-2,3,5,6-tetrafluorophenyl.

15. The method according to claim 10, wherein said 5,10,15,20-tetraaryl-porphyrin compound is selected from the group consisting of the compounds herein designated P15, P16, P17, P18, P19 and P20, namely:

P15 5,10,15,20-tetrakis(2,3,5,6-tetrafluoro-4-trimethylammonio-phenyl)-21H, 23H-methyl-porphine tetra-trifluoromethylsulfonate P16 5-pentafluorophenyl-10,15,20-tris(N-methyl-4-pyridylium)-21H, 23H-porphine triiodide P17 5,15-bis(pentafluorophenyl)-10,20-bis(N-methyl-4-pyridylium)-21H, 23H-porphine diiodide P18 5,10-bis(pentafluorophenyl)-15,20-bis(N-methyl-4-pyridylium)-21H, 23H-porphine diiodide P19 5,10,15-tris(N-methyl-4-pyridylium)-20-(2,3,5,6-tetrafluoro-4-aminopropyl-amino-phenyl)-21H, 23H-porphine triiodide P20 5,10,15,20-tetrakis[4-(N-methyl-2-pyridylium) 2,3,5,6-tetrafluoro-phenyl]-21H, 23H-porphine tetraiodide.

16. A method according to claim 9 activity which comprises administration of a 5,10,15-triaryl-corrole of the formula:

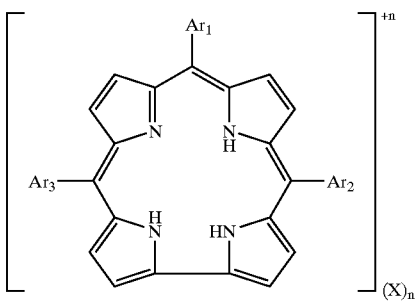

wherein Ar₁, Ar₂, and Ar₃, the same or different, are each an aryl radical selected from the group consisting of a carboaryl, a heteroaryl and a mixed carboaryl-heteroaryl radical, wherein said carboaryl radical by itself or as part of a mixed carboaryl-heteroaryl radical is selected from the group consisting of phenyl, biphenyl and naphthyl substituted by one or more halogen atoms, and/or one or more $C_1$–$C_8$ alkyl, $C_1$–$C_8$ alkoxy, $C_1$–$C_8$ alkylamino, amino-($C_1$–$C_8$)alkylamino, and tri-($C_1$–$C_8$) alkylammonium radicals, and said heteroaryl radical by itself or as part of a mixed carboaryl-heteroaryl radical is selected from the group consisting of furyl, thienyl, pyrrolyl, imidazolyl, thiazolyl, pyridyl, pyrimidyl, and triazinyl substituted by one or more halogen atoms, and/or one or more $C_1$–$C_8$ alkyl, $C_1$–$C_8$ alkoxy, $C_1$–$C_8$alkylamino, amino-($C_1$–$C_8$) alkylamino, and tri-($C_1$–$C_8$) alkylammonium radicals, and wherein at least two of said aryl radicals are positively charged, n is an integer from 2 to 3 and X is a pharmaceutically acceptable anion, in an amount sufficient to inhibit said growth factor receptor tyrosine kinase activity.

17. The method according to claim 16, wherein said carboaryl radical is phenyl substituted by fluoro and optionally by tri-($C_1$–$C_8$) alkylammonium or amino-($C_1$–$C_8$) alkylamino.

18. The method according to claim 16, wherein one or two of said carboaryl radicals is pentafluorophenyl and/or 4-aminopropylamino-2,3,5,6-tetrafluorophenyl.

19. The method according to claim 17, wherein one to three of said carboaryl radicals is 4-trimethylammoniophenyl or 4-trimethylammonio-2,3,5,6-tetrafluorophenyl.

20. The method according to claim 16, wherein said one to three of said heteroaryl radicals is N-($C_1$–$C_8$alkyl)-pyridylium.

21. The method according to claim 20, wherein said radical is selected from the group consisting of 2-, 3- and 4-(N-methyl) pyridylium.

22. The method according to claim 16, wherein said mixed carboaryl-heteroaryl radical is 4-(N-methyl-2-pyridylium)-2,3,5,6-tetrafluorophenyl.

23. The method according to claim 16 wherein the 5,10,15-triaryl-corrole is 5,10,15-tris[2,3,5,6-tetrafluorophenyl-4-(N-methyl-2-pyridylium)]-21H,23H-corrole triiodide.

24. The method according to claim 9, wherein said growth factor receptor tyrosine kinase is selected from the group consisting of fibroblast growth factor (FGF) receptor tyrosine kinase, epidermal growth factor (EGF) receptor tyrosine kinase, heparin-binding EGF-like growth factor (HB-EGF) receptor tyrosine kinase, platelet derived growth factor (PDGF) receptor tyrosine kinase, vascular endothelial growth factor (VEGF) receptor tyrosine kinase, nerve growth factor (VGF) receptor tyrosine kinase, hepatocyte growth factor (HGF) receptor tyrosine kinase, insulin receptor tyrosine kinase and insulin-like growth factor (IGF) receptor tyrosine kinase.

25. The method according to claim 9, wherein said patient in need is one in need of: (i) inhibition of angiogenesis; (ii) inhibition of vascular smooth muscle cell proliferation in disorders selected from the group consisting of atherosclerosis, hyperthrophic heart failure and postsurgical restenosis; (iii) inhibition of cell proliferation and migration in the treatment of primary tumors and metastasis; (iv) treatment of nonmalignant tumors; (v) treatment of diabetic retinopathy, psoriasis, rheumatoid arthritis, retrolental fibroplasia, macular degeneration, hemangioma, arteriovenous malformation, hypertrophic scars, acne, scleroderma and autoimmune diseases; or (vi) treatment of bone and cartilage related disorders and inherited skeletal disorders selected from the group consisting of achondroplasia, dwarfism and craniosynostosis.

26. The method according to claim 25, wherein said patient in need is one in need of inhibition of angiogenesis, and wherein said tetropyrrolic macrocycle is 5,10,15-tris[2,3,5,6-tetrafluorophenyl-4-(N-methyl-2-pyridylium]-21H,23H-corrole triiodide, administered in an amount sufficient to effect said inhibition.

27. The method according to claim 25, wherein said patient in need is one in need of inhibition of vascular smooth muscle cell proliferation in postsurgical restenosis, and wherein said tetropyrrolic macrocycle is 5,10,15,20-tetrakis(N-methyl-4-pyridylium)-21H,23H-porphine tetra-p-tosylate or 5,10,15,20-tetrakis[4-(N-methyl-2-pyridylium) 2,3,5,6-tetrafluoro-phenyl]-21H,23H-porphine tetraiodide, administered in an amount sufficient to effect said inhibition.

28. The method according to claim 25, wherein said patient in need is one in need of inhibition of cell proliferation and migration in the treatment of primary tumors and metastasis, and wherein said tetropyrrolic macrocycle is 5,10,15-tris[2,3,5,6-tetrafluorophenyl-4-(N-methyl-2-pyridylium)]-21H,23H-corrole triiodide, administered in an amount sufficient to effect said inhibition.

29. The method according to claim 25, wherein said patient in need is one in need of inhibition of FGFR-3 tyrosine kinase activity and treatment of achondroplasia, and wherein said tetropyrrolic macrocycle is 5-pentafluorophenyl-10,15,20-tris(N-methyl-4-pyridylium)-21H,23H-porphine triiodide, administered in an amount sufficient to effect said inhibition.

30. A method for inhibiting angiogenesis, comprising administering an inhibitor which is a tetrapyrrolic macrocycle selected from the group consisting of:
(a) a 5,10,15,20-tetraaryl-porphyrin of the formula:

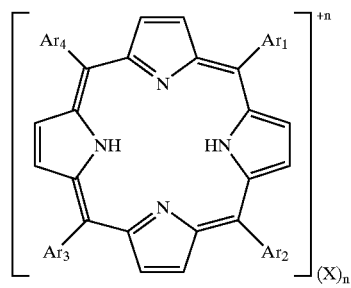

wherein Ar₁, Ar₂, Ar₃, and Ar₄, the same or different, are each an aryl radical selected from the group consisting of a carboaryl, a heteroaryl and a mixed carboaryl-heteroaryl radical, wherein said carboaryl radical by itself or as part of a mixed carboaryl-heteroaryl radical is selected from the group consisting of phenyl, biphenyl and naphthyl substituted by one or more halogen atoms, and/or one or more $C_1$–$C_8$ alkyl, $C_1$–$C_8$ alkoxy, $C_1$–$C_8$ alkylamino, amino-($C_1$–$C_8$)alkylamino, and tri-($C_1$–$C_8$) alkylammonium radicals, and said heteroaryl radical by itself or as part of a mixed carboaryl-heteroaryl radical is selected from the group consisting of furyl, thienyl, pyrrolyl, imidazolyl, thiazolyl, pyridyl, pyrimidyl, and triazinyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, wherein at least two of said $Ar_1$, $Ar_2$, $Ar_3$, and $Ar_4$ aryl radicals are positively charged, n is an integer from 2 to 4 and X is a pharmaceutically acceptable anion; and (b) 5,10,15-triaryl-corrole of the formula:

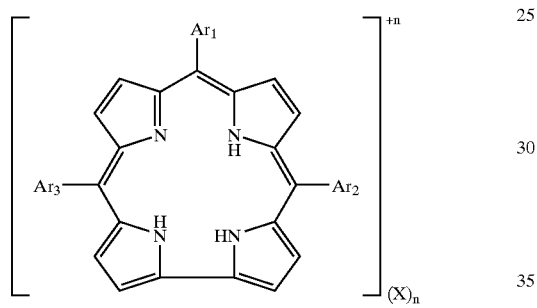

wherein $Ar_1$, $Ar_2$, and $Ar_3$, the same or different, are each an aryl radical selected from the group consisting of a carboaryl, a heteroaryl and a mixed carboaryl-heteroaryl radical, wherein said carboaryl radical by itself or as part of a mixed carboaryl-heteroaryl radical is selected from the group consisting of phenyl, biphenyl and naphthyl substituted by one or more halogen atoms, and/or one or more $C_1$–$C_8$ alkyl, $C_1$–$C_8$ alkoxy, $C_1$–$C_8$ alkylamino, amino-($C_1$–$C_8$)alkylamino, and tri-($C_1$–$C_8$) alkylammonium radicals, and said heteroaryl radical by itself or as part of a mixed carboaryl-heteroaryl radical is selected from the group consisting of furyl, thienyl, pyrrolyl, imidazolyl, thiazolyl, pyridyl, pyrimidyl, and triazinyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, and wherein at least two of said $Ar_1$, $Ar_2$, $Ar_3$ aryl radicals are positively charged, n is an integer from 2 to 3 and X is a pharmaceutically acceptable anion;

in an amount sufficient to inhibit angiogenesis.

31. A method for prevention of restenosis after percutaneous transluminal coronary angioplasty, comprising administering an inhibitor which is a tetrapyrrolic macrocycle selected from the group consisting of:

(a) a 5,10,15,20-tetraaryl-porphyrin of the formula:

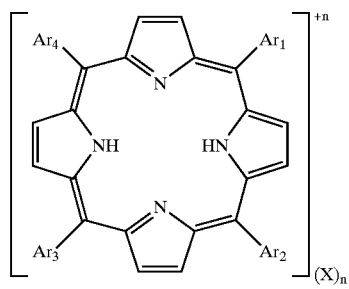

wherein $Ar_1$, $Ar_2$, $Ar_3$, and $Ar_4$, the same or different, are each an aryl radical selected from the group consisting of a carboaryl, a heteroaryl and a mixed carboaryl-heteroaryl radical, wherein said carboaryl radical by itself or as part of a mixed carboaryl-heteroaryl radical is selected from the group consisting of phenyl, biphenyl and naphthyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, and said heteroaryl radical by itself or as part of a mixed carboaryl-heteroaryl radical is selected from the group consisting of furyl, thienyl, pyrrolyl, imidazolyl, thiazolyl, pyridyl, pyrimidyl, and triazinyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, wherein at least two of said $Ar_1$, $Ar_2$, $Ar_3$, and $Ar_4$ aryl radicals are positively charged, n is an integer from 2 to 4 and X is a pharmaceutically acceptable anion; and (b) 5,10,15-triaryl-corrole of the formula:

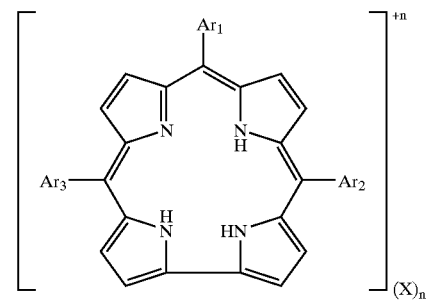

wherein $Ar_1$, $Ar_2$, and $Ar_3$, the same or different, are each an aryl radical selected from the group consisting of a carboaryl, a heteroaryl and a mixed carboaryl-heteroaryl radical, wherein said carboaryl radical by itself or as part of a mixed carboaryl-heteroaryl radical is selected from the group consisting of phenyl, biphenyl and naphthyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, and said heteroaryl radical by itself or as part of a mixed carboaryl-heteroaryl radical is selected from the group consisting of furyl, thienyl, pyrrolyl, imidazolyl, thiazolyl, pyridyl, pyrimidyl, and triazinyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, and wherein at least two of said $Ar_1$, $Ar_2$, $Ar_3$ aryl radicals are positively charged, n is an integer from 2 to 3 and X is a pharmaceutically acceptable anion;

in an amount sufficient to inhibit smooth muscle cell proliferation.

33. A method for inhibition of vascular smooth muscle cell proliferation in disorders selected from the group consisting of atherosclerosis, hyperthrophic heart failure and postsurgical restenosis, comprising the administration of an inhibitor which is a tetrapyrrolic macrocycle selected from the group consisting of:

(a) a 5,10,15,20-tetraaryl-porphyrin of the formula:

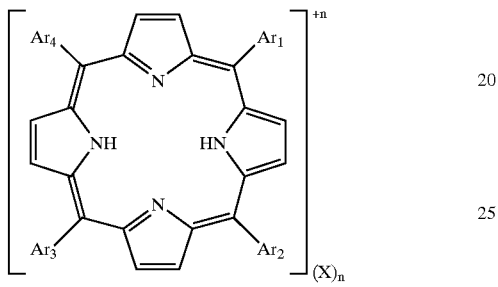

wherein $Ar_1$, $Ar_2$, $Ar_3$, and $Ar_4$, the same or different, are each an aryl radical selected from the group consisting of a carboaryl, a heteroaryl and a mixed carboaryl-heteroaryl radical, wherein said carboaryl radical by itself or as part of a mixed carboaryl-heteroaryl radical is selected from the group consisting of phenyl, biphenyl and naphthyl substituted by one or more halogen atoms, and/or one or more $C_1$–$C_8$ alkyl, $C_1$–$C_8$ alkoxy, $C_1$–$C_8$ alkylamino, amino-($C_1$–$C_8$)alkylamino, and tri-($C_1$–$C_8$) alkylammonium radicals, and said heteroaryl radical by itself or as part of a mixed carboaryl-heteroaryl radical is selected from the group consisting of furyl, thienyl, pyrrolyl, imidazolyl, thiazolyl, pyridyl, pyrimidyl, and triazinyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, wherein at least two of said $Ar_1$, $Ar_2$, $Ar_3$, and $Ar_4$ aryl radicals are positively charged, n is an integer from 2 to 4 and X is a pharmaceutically acceptable anion; and (b) 5,10,15-triaryl-corrole of the formula:

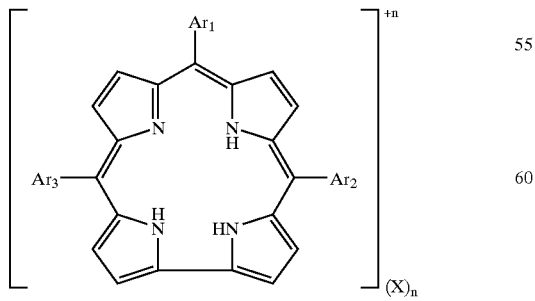

in an amount sufficient to inhibit said vascular smooth muscle cell proliferation.

33. A 5,10,15,20-tetraaryl-porphyrin of the formula:

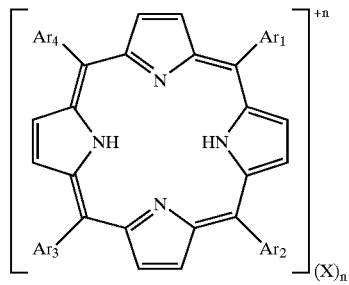

wherein $Ar_1$, $Ar_2$, $Ar_3$, and $Ar_4$, the same or different, are each an aryl radical selected from the group consisting of a carboaryl, a heteroaryl and a mixed carboaryl-heteroaryl radical, wherein said carboaryl radical by itself or as part of a mixed carboaryl-heteroaryl radical is selected from the group consisting of phenyl, biphenyl and naphthyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, and said heteroaryl radical by itself or as part of a mixed carboaryl-heteroaryl radical is selected from the group consisting of furyl, thienyl, pyrrolyl, imidazolyl, thiazolyl, pyridyl, pyrimidyl, and triazinyl substituted by one or more halogen atoms, and/or one or more $C_1$–$C_8$ alkyl, $C_1$–$C_8$ alkoxy, $C_1$–$C_8$ alkylamino, amino-($C_1$–$C_8$) alkylamino, and tri-($C_1$–$C_8$) alkylammonium radicals, wherein at least two of said $Ar_1$, $Ar_2$, $Ar_3$, and $Ar_4$ aryl radicals are positively charged, n is an integer from 2 to 4 and X is a pharmaceutically acceptable anion, provided that at least two of said at least two positively charged $Ar_1$, $Ar_2$, $Ar_3$, and $Ar_4$ aryl radicals are selected from the group consisting of N-($C_1$–$C_8$)alkyl-pyridylium, 4-tri($C_1$–$C_8$)alkylammonium)-2,3,5,6-tetrafluorophenyl and 4-N-($C_1$–$C_8$)alkyl-pyridylium)-2,3,5,6-tetrafluorophenyl and, when at least two of said positively charged $Ar_1$, $Ar_2$, $Ar_3$, and $Ar_4$ radicals are N-($C_1$–$C_8$)alkyl-pyridylium, at least one of the remaining $Ar_1$, $Ar_2$, $Ar_3$, and $Ar_4$ is a non-positively charged aryl radical selected from pentafluorophenyl or 4-amino($C_1$–$C_8$)alkylamino-2,3,5,6-tetrafluorophenyl.

34. The porphyrin of claim 33 being selected from the group consisting of the compounds 5-pentafluorophenyl-10,15,20-tris(N-methyl-4-pyridylium)-21H, 23H-porphine triiodide [P16]; 5,15-bis(pentafluorophenyl)-10,20-bis(N-methyl-4-pyridylium)-21H, 23H-porphine diiodide [P17]; 5,10-bis (pentafluorophenyl)-15,20-bis(N-methyl-4-pyridylium)-21H, 23H-porphine diiodide [P18]; 5,10,15-tris (N-methyl-4-pyridylium)-20-(2,3,5,6-tetrafluoro-4-aminopropyl-amino-phenyl)-21H,23H-porphine triiodide [P19] and 5,10,15,20-tetrakis[4-(N-methyl-2-pyridylium)-2,3,5,6-tetrafluoro-phenyl]-21H, 23H-porphine tetraiodide [P20].

* * * * *